US011806219B2

(12) United States Patent
Kurt et al.

(10) Patent No.: US 11,806,219 B2
(45) Date of Patent: Nov. 7, 2023

(54) SENSOR FOR ABSORBENT ARTICLE

(71) Applicant: Medline Industries, LP, Northfield, IL (US)

(72) Inventors: Alyssa Kurt, Kenosha, WI (US); Amanda Roszkowiak, Schaumburg, IL (US); Kristy Matus, Grayslake, IL (US); Derrick Roemisch, Lindenhurst, IL (US); Karolina Blaszczuk, Des Plaines, IL (US); Michelle Christiansen, McHenry, IL (US); Jeremy Stephen Fogel, Evanston, IL (US); William Bowser, Mundelein, IL (US); Morgan Uridil, Cedar Rapids, IA (US); Cole Fuerste, Evanston, IL (US)

(73) Assignee: Medline Industries, LP, Northfield, IL (US)

( * ) Notice: Subject to any disclaimer, the term of this patent is extended or adjusted under 35 U.S.C. 154(b) by 0 days.

(21) Appl. No.: 17/853,586

(22) Filed: Jun. 29, 2022

(65) Prior Publication Data
US 2022/0323265 A1 Oct. 13, 2022

Related U.S. Application Data

(63) Continuation of application No. 17/549,554, filed on Dec. 13, 2021, which is a continuation of application
(Continued)

(51) Int. Cl.
A61F 13/42 (2006.01)
A61F 13/513 (2006.01)
(Continued)

(52) U.S. Cl.
CPC ............ A61F 13/42 (2013.01); A61F 13/513 (2013.01); A61F 13/51456 (2013.01); A61F 13/53 (2013.01); A61F 2013/424 (2013.01)

(58) Field of Classification Search
CPC ...................................................... A61F 13/42
See application file for complete search history.

(56) References Cited

U.S. PATENT DOCUMENTS 4,834,733 A 5/1989 Huntoon et al.
5,266,928 A 11/1993 Johnson
(Continued)

FOREIGN PATENT DOCUMENTS

WO 2002078513 A2 10/2002
WO 2004021944 A1 3/2004
(Continued)

OTHER PUBLICATIONS

International Search Report and Written Opinion of the International Searching Authority; International Patent Application No. PCT/US2020/062689; Medline Industries, LP (Kurt), dated Mar. 17, 2021.
(Continued)

Primary Examiner — Travis R Hunnings
(74) Attorney, Agent, or Firm — GURR BRANDE & SPENDLOVE, PLLC; Robert Spendlove

(57) ABSTRACT

A sensor for monitoring wetness in a diaper or other absorbent article includes a housing that attaches to the absorbent article. The sensor may include inner and outer housing portions that capture an edge of the absorbent article between the housings. The sensor may include contacts that electrically connect with a pair of contact strips embedded in the absorbent article. The distance between the embedded strips may vary depending on the size of the absorbent article. The sensor may include multiple pairs of contacts that are spaced apart to match the distance between the contact strips for the variously sized absorbent articles. In this way, depending on the pair of contacts connected to the contact strips, the sensor may indicate the size of the absorbent article. The sensor may have a housing with a
(Continued)

cavity and a lid that closes the cavity. The lid may be secured with a latch.

19 Claims, 25 Drawing Sheets

Related U.S. Application Data

No. 17/108,239, filed on Dec. 1, 2020, now Pat. No. 11,229,557, which is a continuation-in-part of application No. 16/702,183, filed on Dec. 3, 2019, now Pat. No. 10,888,467, which is a continuation-in-part of application No. 15/626,729, filed on Jun. 19, 2017, now Pat. No. 10,624,795.

(60) Provisional application No. 62/351,372, filed on Jun. 17, 2016.

(51) Int. Cl.
*A61F 13/53* (2006.01)
*A61F 13/514* (2006.01)

(56) References Cited

U.S. PATENT DOCUMENTS

| | | | |
|---|---|---|---|
| 5,291,181 A | 3/1994 | DePonte | |
| 5,443,082 A | 8/1995 | Mewburn | |
| 5,459,452 A * | 10/1995 | DePonte | A61F 13/42 340/573.5 |
| 5,469,145 A | 11/1995 | Johnson | |
| 5,537,095 A | 7/1996 | Dick et al. | |
| 5,570,082 A | 10/1996 | Mahgerefteh et al. | |
| 5,796,345 A | 8/1998 | Leventis et al. | |
| 5,810,188 A | 9/1998 | Novakoski et al. | |
| 5,838,240 A | 11/1998 | Johnson | |
| 5,868,723 A | 2/1999 | Al-Sabah | |
| 5,903,222 A * | 5/1999 | Kawarizadeh | G01N 27/223 340/573.5 |
| 6,097,297 A | 8/2000 | Fard | |
| 6,373,395 B1 | 4/2002 | Kimsey | |
| 6,384,728 B1 | 5/2002 | Kanor et al. | |
| 6,423,044 B1 * | 7/2002 | Roe | A61L 15/26 604/385.12 |
| 6,559,772 B2 | 5/2003 | Zand et al. | |
| 6,583,722 B2 | 6/2003 | Jeutter et al. | |
| 6,603,403 B2 | 8/2003 | Jeutter et al. | |
| 6,617,488 B1 | 9/2003 | Springer et al. | |
| 6,756,521 B1 | 6/2004 | Breitkopf | |
| 6,774,800 B2 | 8/2004 | Friedman et al. | |
| 6,832,507 B1 | 12/2004 | Van De Berg et al. | |
| 6,870,479 B2 | 3/2005 | Gabriel | |
| 6,970,091 B2 | 11/2005 | Roe | |
| 7,053,781 B1 | 5/2006 | Haire et al. | |
| 7,141,715 B2 | 11/2006 | Shapira | |
| 7,250,547 B1 * | 7/2007 | Hofmeister | G01N 27/121 340/573.5 |
| 7,295,125 B2 | 11/2007 | Gabriel | |
| 7,321,315 B2 | 1/2008 | Brumm | |
| 7,352,286 B2 | 4/2008 | Chan et al. | |
| 7,355,090 B2 | 4/2008 | Ales et al. | |
| 7,394,391 B2 | 7/2008 | Long | |
| 7,477,156 B2 | 1/2009 | Long et al. | |
| 7,498,478 B2 | 3/2009 | Long et al. | |
| 7,642,396 B2 | 1/2010 | Ales et al. | |
| 7,649,125 B2 | 1/2010 | Ales et al. | |
| 7,956,754 B2 | 6/2011 | Long | |
| 7,977,529 B2 | 7/2011 | Bergman et al. | |
| 8,032,426 B2 | 10/2011 | Williams | |
| 8,101,813 B2 | 1/2012 | Ales et al. | |
| 8,112,322 B2 | 2/2012 | Williams | |
| 8,190,495 B1 | 5/2012 | Williams | |
| 8,196,809 B2 | 6/2012 | Thorstensson | |
| 8,237,572 B2 | 8/2012 | Clement et al. | |
| 8,248,249 B2 | 8/2012 | Clement et al. | |
| 8,274,393 B2 | 9/2012 | Ales et al. | |
| 8,314,284 B1 | 11/2012 | Novello | |
| 8,376,232 B2 | 2/2013 | Eckstein | |
| 8,378,167 B2 | 2/2013 | Allen et al. | |
| 8,421,636 B2 | 4/2013 | Collette et al. | |
| 8,431,766 B1 * | 4/2013 | Lonero | A61F 13/42 604/361 |
| 8,471,715 B2 | 6/2013 | Solazzo et al. | |
| 8,604,268 B2 | 12/2013 | Cohen et al. | |
| 8,697,933 B2 | 4/2014 | Ales et al. | |
| 8,698,641 B2 | 4/2014 | Abraham et al. | |
| 8,866,624 B2 | 10/2014 | Ales et al. | |
| 8,871,994 B2 | 10/2014 | Wei et al. | |
| 8,884,769 B2 | 11/2014 | Novak | |
| 8,962,909 B2 | 2/2015 | Groosman et al. | |
| 8,978,452 B2 | 3/2015 | Johnson et al. | |
| 9,107,776 B2 | 8/2015 | Bergman et al. | |
| 9,131,893 B2 | 9/2015 | Faybishenko et al. | |
| 9,132,044 B2 | 9/2015 | Sjoholm et al. | |
| 9,138,354 B2 | 9/2015 | Nhan et al. | |
| 9,160,054 B2 | 10/2015 | Yu et al. | |
| 9,194,833 B2 | 11/2015 | Bosaeus et al. | |
| 9,224,102 B2 | 12/2015 | Barda et al. | |
| 9,241,839 B2 | 1/2016 | Abraham et al. | |
| 9,278,033 B2 | 3/2016 | Abraham et al. | |
| 9,283,123 B2 | 3/2016 | Lewis et al. | |
| 9,291,589 B2 | 3/2016 | Wong et al. | |
| 9,314,381 B2 | 4/2016 | Curran et al. | |
| 9,322,797 B1 | 4/2016 | Lastinger et al. | |
| 9,333,118 B2 | 5/2016 | Elfstrom et al. | |
| 9,366,644 B1 | 6/2016 | Lastinger et al. | |
| 9,646,073 B2 | 5/2017 | Mashin-Chi et al. | |
| 9,665,639 B2 | 5/2017 | Mashin-Chi et al. | |
| 9,713,554 B2 | 7/2017 | Barda et al. | |
| 9,913,608 B2 | 3/2018 | Lewis et al. | |
| D826,740 S | 8/2018 | Stevens et al. | |
| 10,111,590 B2 | 10/2018 | Thoen | |
| 10,624,795 B2 | 4/2020 | Christiansen et al. | |
| 10,713,372 B1 * | 7/2020 | Heyl | G06F 21/00 |
| 10,744,042 B2 | 8/2020 | Park et al. | |
| 2003/0011479 A1 * | 1/2003 | Bluteau | A61F 13/42 340/573.5 |
| 2003/0060789 A1 * | 3/2003 | Shapira | A61F 13/42 604/362 |
| 2004/0030309 A1 * | 2/2004 | Huang | A61F 13/15585 604/361 |
| 2004/0078014 A1 * | 4/2004 | Shapira | A61F 13/84 604/361 |
| 2004/0100376 A1 | 5/2004 | Lye et al. | |
| 2004/0113801 A1 * | 6/2004 | Gustafson | A61F 13/2051 340/573.5 |
| 2004/0207530 A1 * | 10/2004 | Nielsen | A61F 13/42 340/573.5 |
| 2004/0230172 A1 * | 11/2004 | Shapira | A61F 13/84 604/361 |
| 2007/0252710 A1 | 11/2007 | Long et al. | |
| 2007/0282286 A1 * | 12/2007 | Collins | A61F 13/42 604/361 |
| 2008/0058740 A1 * | 3/2008 | Sullivan | A61F 13/42 604/361 |
| 2008/0266123 A1 * | 10/2008 | Ales | A61F 13/42 343/720 |
| 2008/0269702 A1 * | 10/2008 | Ales | A61F 13/42 604/361 |
| 2009/0326417 A1 | 12/2009 | Ales, III et al. | |
| 2010/0089264 A1 | 4/2010 | Warner | |
| 2010/0168694 A1 | 7/2010 | Gakhar et al. | |
| 2011/0234412 A1 * | 9/2011 | Bhatia | A61F 13/42 340/573.5 |
| 2011/0295619 A1 | 12/2011 | Tough | |
| 2012/0161960 A1 | 6/2012 | Cheng et al. | |
| 2012/0172825 A1 | 7/2012 | Ales | |
| 2012/0173249 A1 | 7/2012 | Popp | |
| 2013/0052432 A1 | 2/2013 | Koebel | |
| 2013/0110063 A1 * | 5/2013 | Abraham | G16H 40/67 604/361 |
| 2013/0345657 A1 | 12/2013 | Nelson | |

(56) References Cited

U.S. PATENT DOCUMENTS

| | | |
|---|---|---|
| 2014/0063085 A1 | 3/2014 | Warner |
| 2014/0155850 A1* | 6/2014 | Shah ................... A61F 13/42 604/361 |
| 2014/0198203 A1 | 7/2014 | Vardi et al. |
| 2015/0080819 A1 | 3/2015 | Charna et al. |
| 2015/0157251 A1* | 6/2015 | Nelson ............ A61B 5/14507 600/580 |
| 2016/0267769 A1 | 9/2016 | Rokhsaz et al. |
| 2016/0338883 A1 | 11/2016 | Meek et al. |
| 2016/0361209 A1 | 12/2016 | Mashin-Chi et al. |
| 2017/0000655 A1 | 1/2017 | Mashin-Chi et al. |
| 2017/0258643 A1* | 9/2017 | Xu ........................ A61F 13/42 |
| 2017/0360623 A1 | 12/2017 | Christiansen et al. |
| 2018/0082035 A1 | 3/2018 | Collette et al. |
| 2018/0104115 A1 | 4/2018 | Collette et al. |
| 2018/0177644 A1* | 6/2018 | Tuli ....................... A61F 13/42 |
| 2018/0256412 A1* | 9/2018 | Love ................. A61F 13/0209 |
| 2018/0325743 A1* | 11/2018 | Ho ........................ A61F 13/42 |
| 2019/0051137 A1* | 2/2019 | Kilcran ................. A61F 13/42 |
| 2019/0070043 A1 | 3/2019 | Collette |
| 2019/0287678 A1* | 9/2019 | Stevens ................. A61B 5/746 |
| 2019/0388029 A1 | 12/2019 | Stevens et al. |
| 2020/0093411 A1 | 3/2020 | Stevens et al. |
| 2020/0163808 A1* | 5/2020 | Grudno ................ G01N 27/223 |
| 2020/0276063 A1* | 9/2020 | Muñoz Herencia .... A61F 13/58 |

FOREIGN PATENT DOCUMENTS

| | | |
|---|---|---|
| WO | 2006058276 A2 | 6/2006 |
| WO | 2007125446 A1 | 11/2007 |
| WO | 2008130298 A1 | 10/2008 |
| WO | 2016116106 A1 | 7/2016 |
| WO | 2018098300 A1 | 5/2018 |
| WO | 2019225854 A1 | 11/2019 |
| WO | 2019246347 A1 | 12/2019 |
| WO | 2021113230 A1 | 6/2021 |

OTHER PUBLICATIONS

International Search Report and Written Opinion of the International Searching Authority; International Application No. PCT/US2017/038146; Medline Industries, LP (Christiansen), dated Oct. 30, 2017.

Supplementary European Search Report; European Application No. 17814259; Medline Industries, LP (Christiansen), dated Feb. 10, 2020.

* cited by examiner

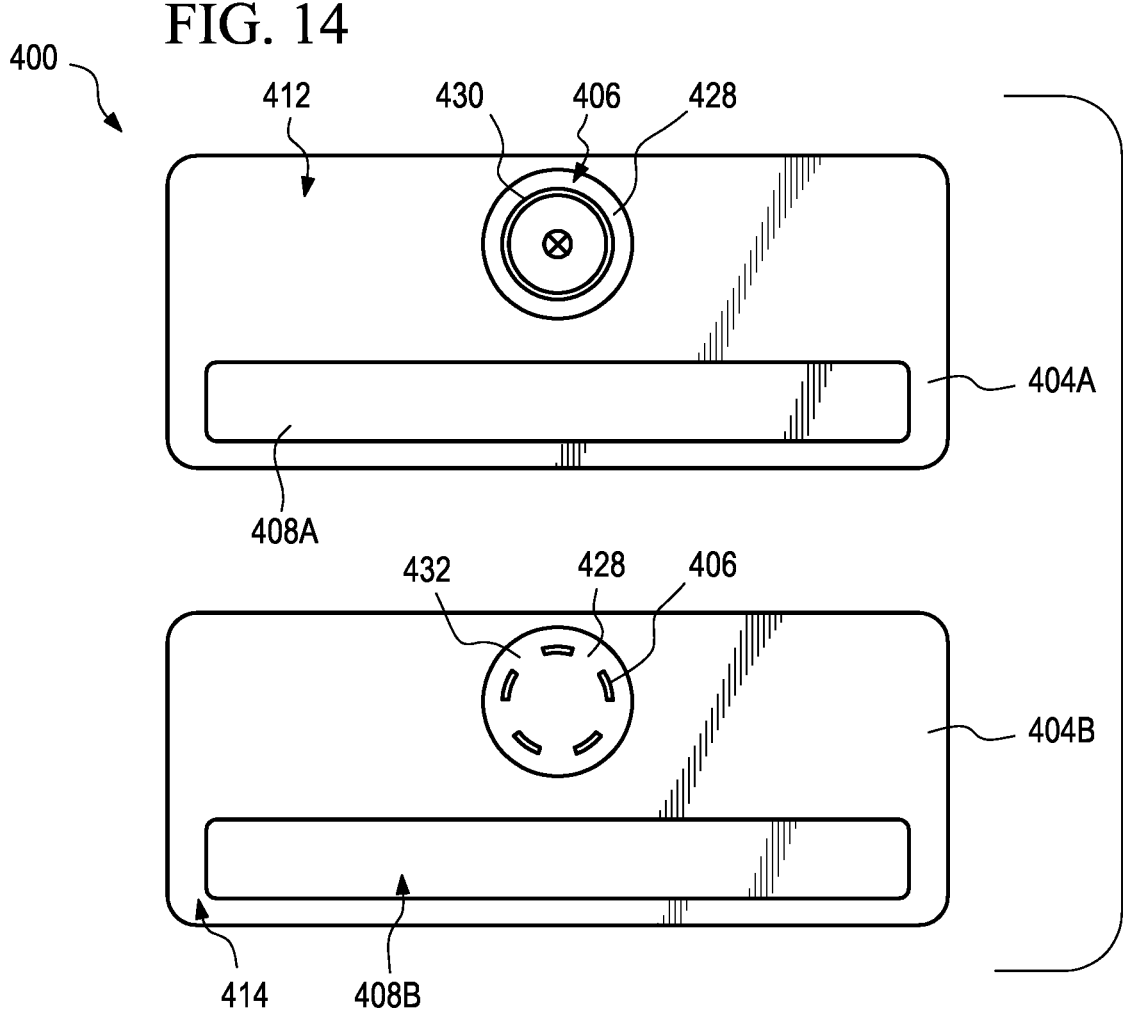
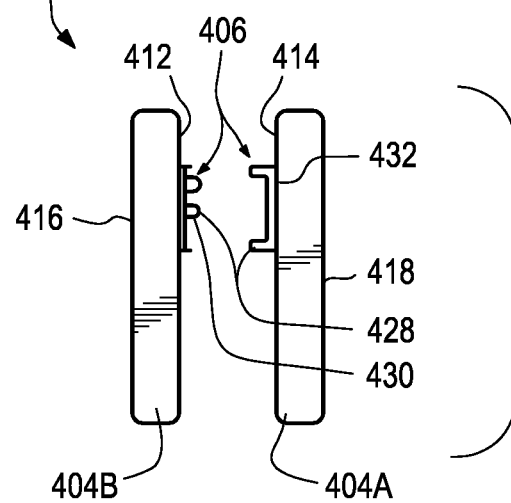

SENSOR FOR ABSORBENT ARTICLE

CROSS-REFERENCE TO RELATED APPLICATIONS

This application is a continuation of U.S. patent application Ser. No. 17/549,554 filed Dec. 13, 2021 entitled "SENSOR FOR ABSORBENT ARTICLE," which application is a continuation of U.S. patent application Ser. No. 17/108,239 filed Dec. 1, 2020 and issued as U.S. Pat. No. 11,229,557 entitled "SENSOR FOR ABSORBENT ARTICLE," which application is a continuation-in-part of U.S. patent application Ser. No. 16/702,183 filed 3 Dec. 2019 and issued as U.S. Pat. No. 10,888,467 on 12 Jan. 2021 entitled "SENSOR FOR ABSORBENT ARTICLE," which application is a continuation-in-part of U.S. patent application Ser. No. 15/626,729 filed 19 Jun. 2017 and issued as U.S. Pat. No. 10,624,785 on 21 Apr. 2020 entitled "SENSOR FOR ABSORBENT ARTICLE," which application claims priority to U.S. Provisional Application No. 62/351,372 filed on 17 Jun. 2016 and entitled "SENSOR FOR ABSORBENT ARTICLE," the contents of each of which are incorporated herein by reference.

FIELD OF THE INVENTION

The present invention relates generally to absorbent articles and, in particular, to the use of wetness sensors.

BACKGROUND

Millions of people of all ages suffer from incontinence of the bowel or bladder. Whether an infant, adult, or elderly person, the underlying cause of incontinence varies but the method of treatment typically involves absorbent article products. Adult incontinent briefs, disposable diapers, pull-up diapers, protective underwear and underpads can alleviate some of the emotional and physical discomfort of incontinence by absorbing and containing liquid and other discharges from the human body to prevent body and clothing soiling.

Typical absorbent articles include a topsheet facing the wearer that permits fluid exudates to pass through and a backsheet that prevents the exudates from escaping from the absorbent article. Much advancement has been made in the art since the introduction of the disposable absorbent article, as shown, for example, in applicant's co-owned U.S. Pat. No. 10,117,792, which is incorporated by reference herein. However, quality care for patients and other users of absorbent articles requires that the article be changed after being wetted, and most of these articles are not adapted to aid the caregiver in the monitoring of the status of the article.

A number of devices and wetness detecting systems have been attempted to report when a diaper, bedding, or adult incontinence article becomes wet due to incontinence. For example, U.S. Pat. No. 8,421,636, which is incorporated herein by reference, describes a patient monitoring system that detects wetness in an absorbent article. However, such devices may be improved in various ways as set forth herein.

BRIEF DESCRIPTION OF THE DRAWINGS

Advantages of the invention will become apparent upon reading the following detailed description and upon reference to the drawings.

FIG. 14 is a plan view of two inner surfaces of an indicator device with a snap feature securement mechanism and conductive plates.

FIG. 15 is a side elevation view of an indicator device with a snap feature securement.

Figure 1:
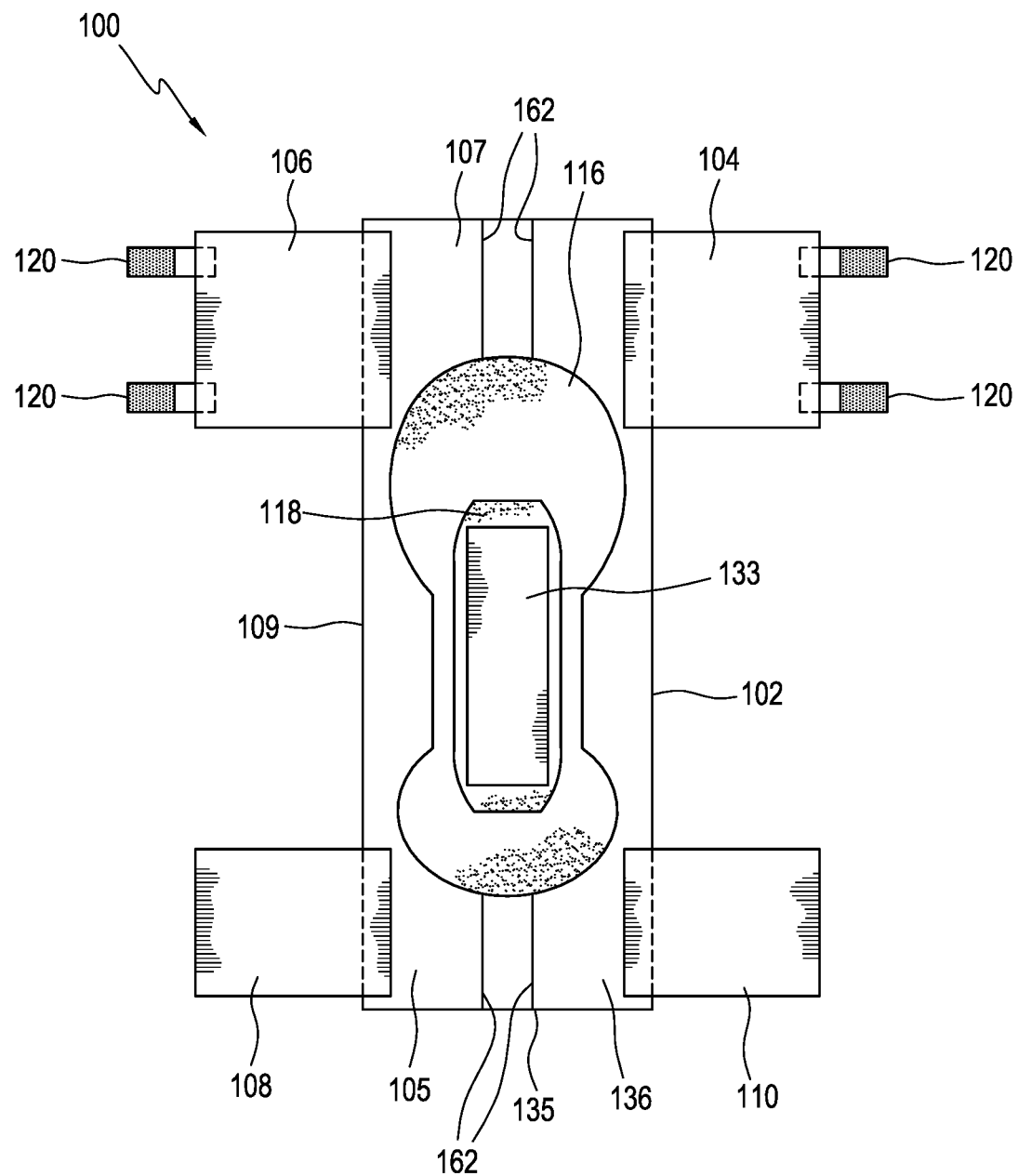
FIG. 1 is a top plan view of an absorbent article in a substantially flat un-contracted position according to one embodiment of the invention.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, forward and rearward, and the like may be used solely to distinguish one entity or action from another entity or action without necessarily requiring or implying any actual such relationship, direction or order between such entities or actions.

Absorbent articles as described herein generally include a moisture-pervious inner layer, an absorbent layer, and a moisture-impervious outer layer. Although the remainder of the description will be specifically directed to adult incontinence articles, such as disposable diapers, it is to be understood that the embodiments may also be implemented using other absorbent articles and that the properties and uses described below apply to these other absorbent articles as well. Throughout this application, the terms absorbent article and diaper are used interchangeably. However, it should be understood that the term diaper is intended to include other absorbent articles, such as training pants, incontinence pads, etc., as would be understood by one of ordinary skill in the art. The terms user and patient are also used interchangeably to indicate a person on whom a diaper is placed.

Figure 2:
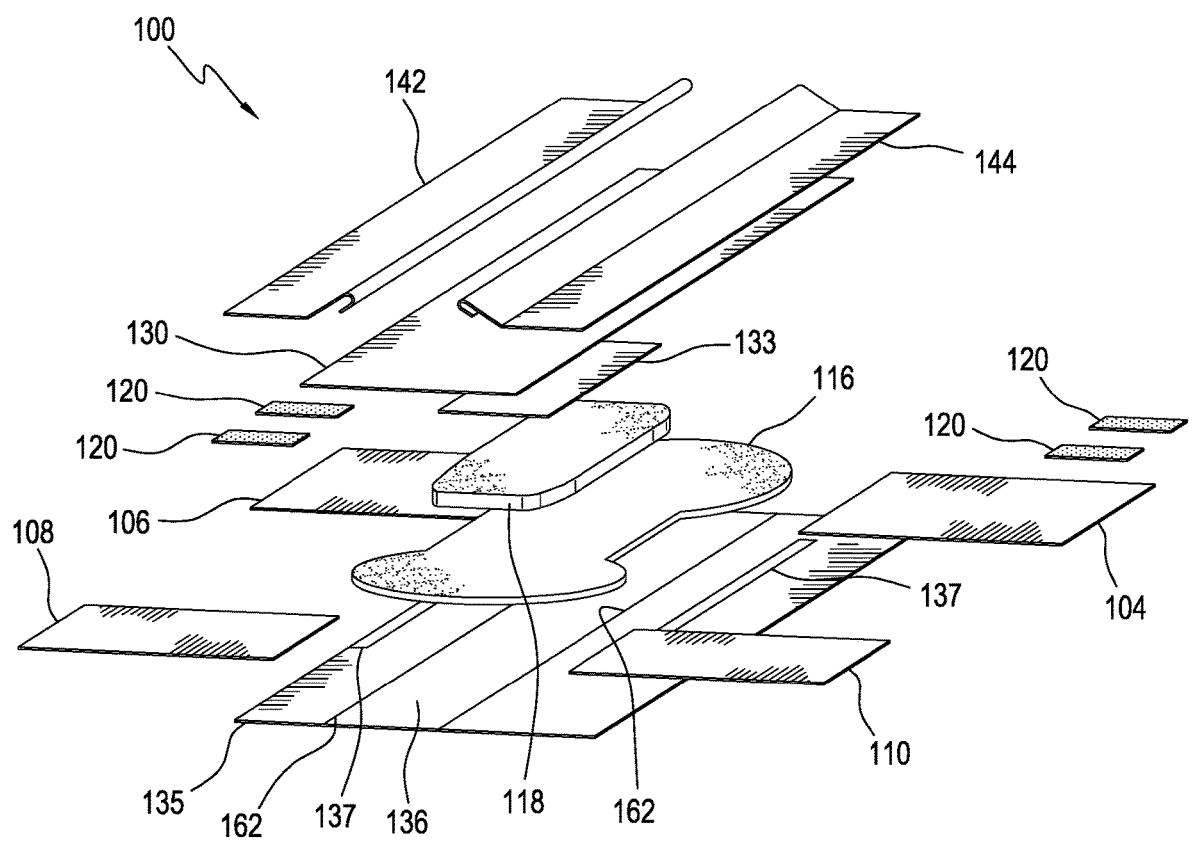
FIG. 2 is an exploded perspective view of the absorbent article of FIG. 1, again in a substantially flat un-contracted position.

FIGS. 1 and 2 illustrate an exemplary non-limiting general embodiment of an absorbent article 100. FIG. 1 illustrates a plan view of the absorbent article 100 in a substantially flat un-contracted state. As shown in these figures, the absorbent article 100 generally consists of several layers, including an inner layer, an absorbent layer, and an outer layer. The inner layer faces a wearer and contacts the skin of the wearer when the absorbent article 100 is secured to the wearer. The inner layer may comprise a topsheet 130 that is composed of a moisture-pervious fabric suitable to allow bodily discharge to pass through the inner layer and be absorbed by the absorbent layer. Non-limiting examples of materials suitable to form the topsheet 130 include polypropylene, polyethylene, polyester, materials having hydrophobic properties, combinations thereof and/or the like. Additionally, the topsheet can be treated with a hydrophilic finish to improve pass through of liquids to diaper layers beneath the inner layer. Non-limiting examples of suitable hydrophilic finishes include stearic acid, melamine-based chemicals, fluorocarbon chemicals, and silicon based chemicals.

The plan view of FIG. 1 is shown from the top or patient contacting side of the absorbent article. The topsheet (130) and other components have been removed for clarity. FIG. 2 is an exploded perspective view of the absorbent article 100. Again, the article 100 is shown in a substantially flat un-contracted state with certain items removed for clarity.

As shown in FIG. 1, an embodiment of the absorbent article 100 comprises a chassis 102. The chassis 102 includes a front waist region 105, a back waist region 107, and a crotch region 109 that is disposed longitudinally between the front and back waist regions 105 and 107. The front waist region 105 and the back waist region 107 generally comprise those portions of the absorbent article 100 which, when worn, encircle the waist of the wearer. The crotch region 109 is that portion of the absorbent article 100 which, when the absorbent article 100 is worn, is generally positioned between the legs of the wearer.

The chassis 102 has a shape such that its outer perimeter is rectangular or at least substantially rectangular in the illustrative embodiment of the absorbent article 100. In other embodiment, there may be portions of the chassis that are shaped and/or removed, such as in the crotch region 109, for example, resulting in a narrower crotch region portion 109 to provide a contoured fit between the legs. Still other embodiments have different shaped chassis, such as hourglass shapes, T-shapes, and the like.

Rear side panels 104, 106 are coupled to and may extend from the back waist region 105. The disposable article may further include front side panels 108, 110 that are coupled to and may extend from the front waist region 105. The back region 107 is generally positioned against the back of the user. The front region 105 is generally positioned against the front of the user. The rear side panels 104, 106 are configured to wrap around a wearer's waist from back to front, extending from each side of the back waist region 105. The front side panels 108, 110 are configured to wrap around a wearer's waist from front to back. In this manner, rear side panel 106 can be connected to front side panel 108 and rear side panel 104 can be connected to front side panel 110 to couple the front region 105 to the back region 107. In this embodiment there are four side panels 104, 106, 108, 110. However, it should be recognized that other embodiments may be configured with more or fewer side panels. In particular, rear side panels 104, 106 may connect directly to an outside surface of front waist region 105 rather than to front side panels 108, 110.

The side panels may attach to the chassis 102 in a variety of manners as would be apparent to one of skill in the art. For example, as described in applicant's co-pending U.S. patent application Ser. No. 13/832,965. Alternatively, one or more of the side panels may be integrally formed, in whole or in part, with a backsheet 135 or topsheet 130 of the absorbent article. The backsheet 135 will have an outside surface 134 facing away from the patient wearing the absorbent article and an inside surface 136 facing toward the patient.

The rear side panels 104, 106 may also include fasteners 120. Fasteners 120 may comprise adhesive tape, hook and loop, snaps or any other appropriate fasteners as would be understood by one of ordinary skill in the art. As shown in the illustrative embodiment, rear side panel 104, 106 includes two fasteners 120. In a preferred embodiment, fasteners 120 can be configured to operatively couple rear side panels 104, 106 to a front region 105 of the diaper chassis 102. Alternative, fasteners 120 may also engage front side panels 108, 110 to attach rear side panels 104, 106, respectively. While FIG. 1 depicts rear side panels 104, 106 as including two fasteners 120, in some embodiments, more or fewer fasteners may be used. While FIG. 1 depicts fasteners 120 sized and shaped a particular way, in other embodiments, fasteners 120 can be a different size and/or shape. Alternatively, the front side panels 108, 110 may include fasteners in additions to, or in place of, the fasteners 120 attached to rear side panels 104, 106.

In another embodiment, the front region 105 and/or front panels 108, 110 may include added or modified features to reinforce or increase the affinity to the fastening device. Additionally, features may be employed to allow adhesive fasteners to be attached and detached from the fastening region multiple times. Those skilled in the art will recognize that there are multiple approaches to doing so via modification of the base material as well as additions of various materials. For example, fasteners 120 may incorporate the hook component of a hook-and-loop closure and portions of the front region 105 and/or front panels 108, 110 may be comprise a corresponding loop component. The surface of front region 105 and/or front panels 108, 110 may be treated to increase or decrease the affinity for the hook components. Alternatively, separate loop component material may be adhered to the surface of the front region 105 and/or front panels 108, 110.

Referring again FIGS. 1 and 2, embodiments of the absorbent article 100 include an absorbent layer. The absorbent layer may comprise an acquisition and/or distribution ("A/D") layer 133, a first absorbent core 116, and a second absorbent core 118.

The liquid acquisition and/or distribution layers serves to rapidly acquire and then distribute acquired liquid to an absorbent core for retention. To achieve rapid acquisition and distribution, these layers often include cellulosic fibers. These layers can include cross-linked cellulosic fibers to impart bulk and resilience to the layer, and wood pulp fibers to increase the wicking of liquid within the layer and to facilitate distribution of the liquid throughout the layer and ultimately to another layer, such as a storage layer, that is in liquid communication with the distribution layer.

Figure 3:
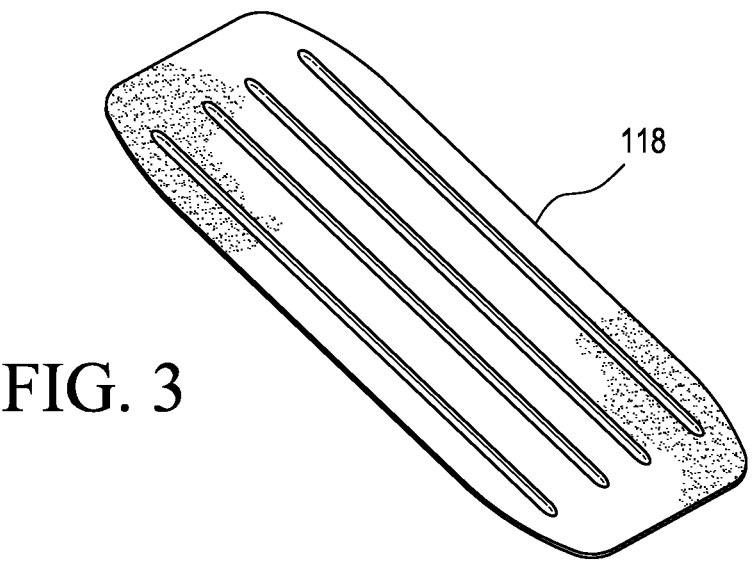
FIG. 3 is a perspective view of a second absorbent core of the absorbent article depicted in FIG. 1.
Figure 4:
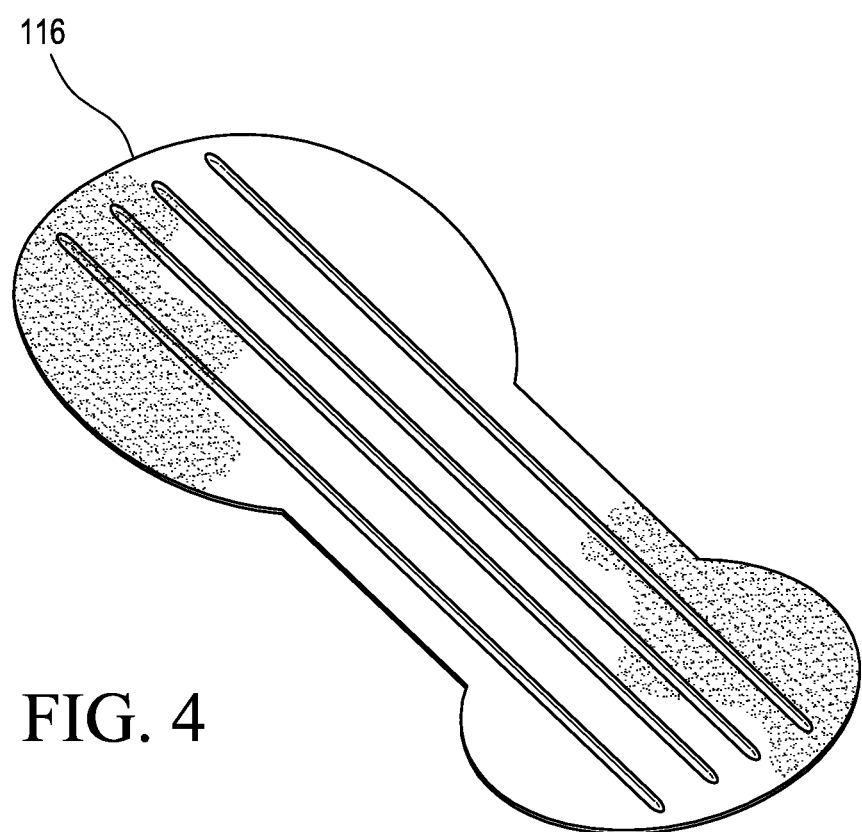
FIG. 4 is a perspective view of a first absorbent core of the absorbent article depicted in FIG. 1.

FIG. 3 is a perspective view of a top (facing towards wearer) of the second core 118, and FIG. 4 is a perspective view of a bottom side (facing away from a wearer) of the first core 116. Each of the first core 116 and second core 118 can be composed of similar material, and can be shaped depending on the size of the absorbent article, and whether it is intended for use by infants, children and/or adults. By way of example, and as shown in FIGS. 3 and 4, first core 116 can be larger and substantially hourglass shaped, whereas second core 118 can be smaller, relative to first core 116, and can be substantially rectangular shaped. In this manner, the absorbent article can include a large surface area of coverage provided by the first core 116, and the increased absorbency provided by the second core 118, without the additional bulk of a second core having the same size as the first core.

First core 116 is shown having an embossed bottom and second core 118 is shown having an embossed top. The embossed top of second core 118 and the embossed bottom of first core 116 provide increased longitudinal flow while reducing lateral flow, and, in this manner, reducing leakage. Said another way, the embossed top of second core 118 and the embossed bottom of first core 116 allows fluid to move longitudinally towards the front and the back of a wearer, as opposed to towards the legs of a wearer.

Each of the first core 116 and the second core 118 may be composed of any materials suitable for absorbing the fluids and discharge including, but not limited to, a fibrous material (e.g., fluffed wood pulp), a super absorbent polymer ("SAP"), or the combination of SAP and fibrous material. The SAP can be natural or synthetic and may be biodegradable. Non-limiting examples of SAP include polymers based on acrylate(s) such as sodium acrylate, potassium acrylate, and/or an alkyl acrylate(s) (e.g., methyl acrylate, ethyl acrylate, propyl acrylate, butyl acrylate, and hexyl acrylate). The absorbency of the diaper may vary depending upon whether it is intended for use by infants, children and/or adults.

While FIGS. 3 and 4 depict the first core 116 having an embossed bottom, and the second core 118 having an embossed top, in some embodiments, an absorbent article can have only a single core with no embossing, a single core with embossing on both, and/or other combinations of one or two cores each with embossing on one, both, or neither side. While the figures show absorbent articles include one or two cores, in some embodiments, absorbent articles can include more or fewer cores.

FIGS. 3 and 4 depict embossing as including four spaced apart embossing "lines," in some embodiments. However, a core can include more or fewer embossing lines. In some embodiments, embossing lines can be adjacent one another, or can be a combination of adjacent and space apart embossing line. In this manner, the different combinations of embossing lines can define an embossing pattern. While FIGS. 3 and 4 depict embossing substantially along the entire width and length of each respective core, in some embodiments a core can have embossing substantially along an entire width and/or length, and/or a portion of a width and/or length.

In embodiments of the invention, the first 116 and second 118 cores may be created with or without the use of super absorbent polymer (SAP). While some literature indicates that the presence of SAP in a diaper used for urine testing is considered benign, manufacturing diapers without SAP for the benefit of accuracy is contemplated by the present invention and may be considered beneficial.

Returning to FIGS. 1 and 2, the absorbent article 100 may further include a set of leak guards and/or a set leg cuffs 142, 144, both known to those of ordinary skill in the art. Additionally, the exemplary absorbent article includes an outer layer or backsheet 135 and elastic bands 137. The elastic bands 137 can by used to gather the leg of the article around the user's leg, improving the fit of the absorbent article 100 and can improve the comfort of the wearer. Elastic bands and other elastic materials may be used at other places in the absorbent article in order to improve the fit and/or fluid retention of the article.

In further embodiments of the invention, the absorbent article includes a sensor system. The sensor system may function to sense a level of wetness and provide a means of measuring that wetness. The sensor system may comprise two metal strips 162 placed between the topsheet 130 and backsheet 135 of the diaper. The strips 162 may be placed adjacent a top surface of the backsheet 135 below the absorbent core 116.

Both the dimension of the strips and distance between the strips are calculated to provide appropriate and uniform resistance changes when they become wet with urine. The saline urine forms a resistive link between the strips of metal and this resistance is input into a comparator circuit to produce an appropriate output. The metal used may be aluminum because of its cost and ease and variety of manufacture. However, any metal capable of sensing and providing a changing resistance could be also used. In addition to metal, any conductive fiber that provide the same function could be used, including for example, a combination stainless steel and nylon thread in a sewn application. The metal strips 162 may include a Mylar support backing to provide additional strength during manufacture and application.

Figure 5:
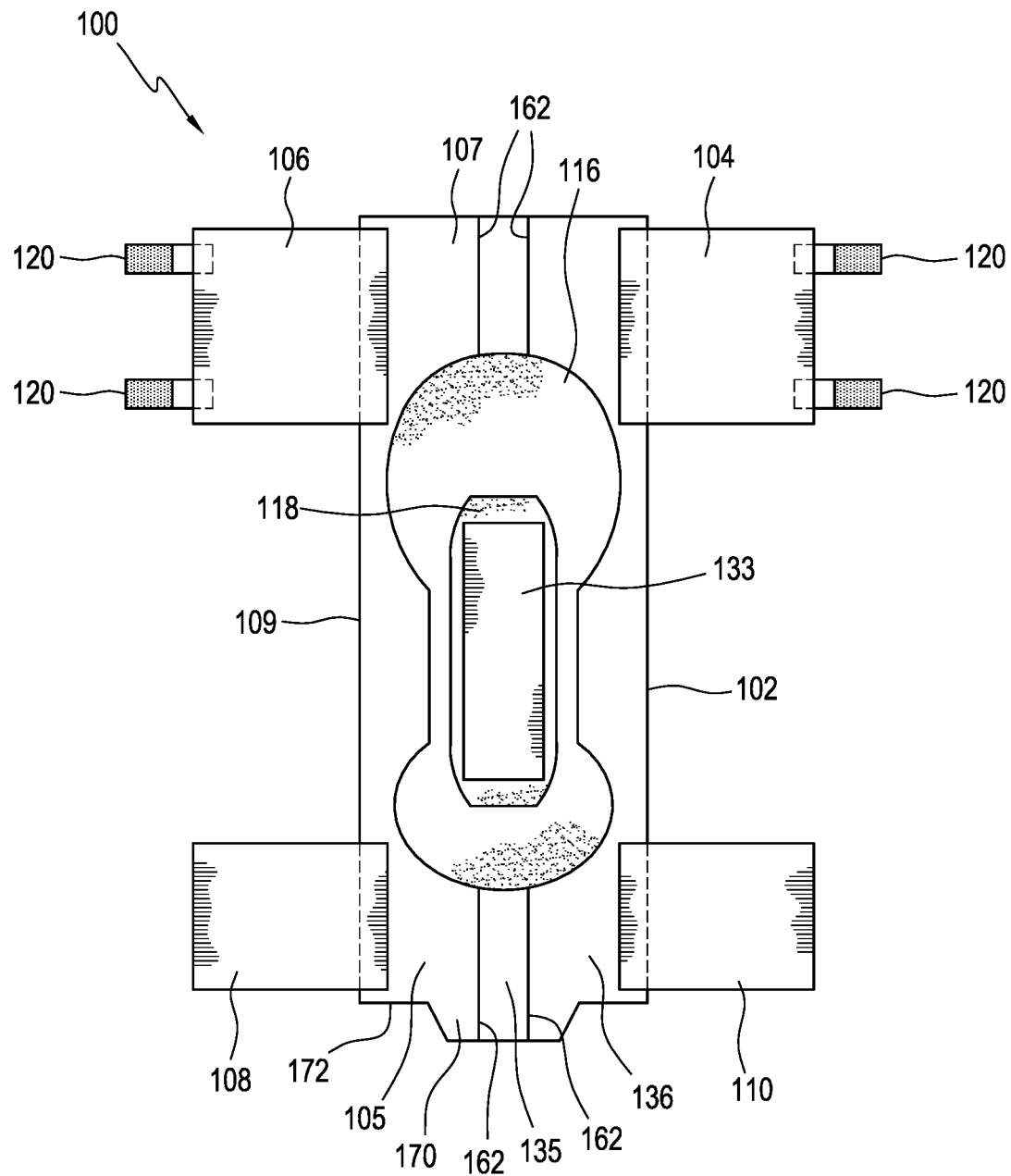
FIG. 5 is a top plan view of an absorbent article in a substantially flat un-contracted position according to a further embodiment of the invention.

As illustrated in FIG. 5, a front portion 105 of the diaper chassis 102 may have a tab 170 that extends beyond the front edge 172 of the diaper. The tab 170 may be formed by an extension of the backsheet 135 or may be a separate portion. The strips 162 extend onto the tab 170. Alternatively, the tab may be formed at a back portion 107 of the diaper.

Figure 6:
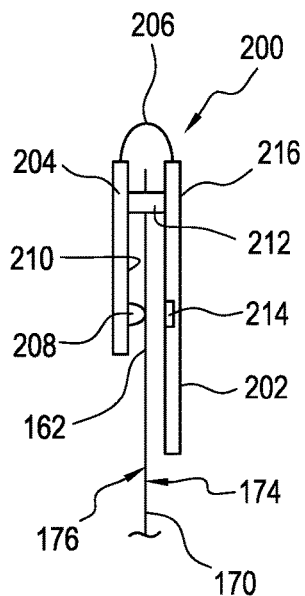
FIG. 6 is a schematic side view of an indicator device of a sensor system in accordance with an embodiment of the invention.
Figure 7:
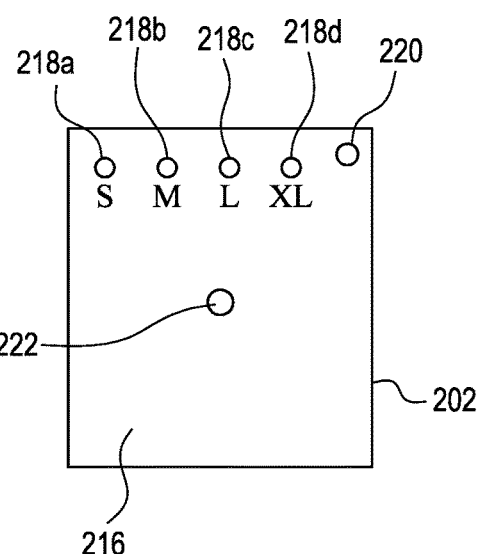
FIG. 7 is a view of a front surface of an outer housing of the indicator device depicted in FIG. 6.
Figure 8:
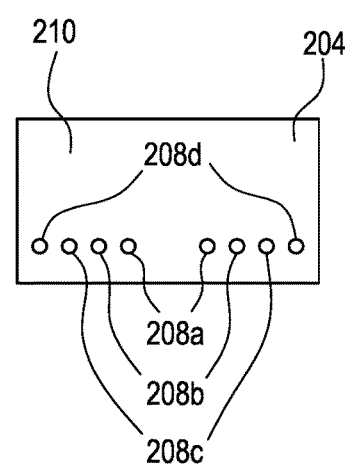
FIG. 8 is a view of an inner housing of the indicator device depicted in FIG. 6.

As illustrated in FIGS. 6-8, the sensor system may further comprise an indicator device 200, which may be in the form of a clip or other means of securing a sensor to a disposable article. FIG. 6 shows a cross sectional view of the diaper tab portion 170, having an inner surface 174 and an outer surface 176. The indicator device 200 may be attached to the tab 170 and include an outer housing 202, and inner housing 204 and a hinge portion 206. Alternatively, the indicator device may be attached to another portion of the diaper such as the back portion 107 or front portion 105 if the diaper does not have tab 170.

Pins 208 may extend from the inner housing 204 to contact strips 162 that extend onto the tab 170. Alternatively, the pins may extend from the outer housing 202. For example, the outer housing 202 may include a PC board with the pins extending slightly through the back of the PC board, such that when they are soldered they will form pin prick contact points. The contact points will penetrate an outside surface 174 of the tab 170 and will contact the strips 162. Holes 214 may be formed on the opposite housing to the pins 208 such that the pins pass through the tab 170 and into the holes. In alternative embodiments, pins 208 will pass through the tab 170 and into recesses, slots indentations or other appropriate structures on the surface of the opposite housing. Wires may connect pins 208 with electronic components positioned within the outer housing 202.

A fastener 212 may extend between the inner 202 and outer 204 housings. The fastener serves to secure the housings to the diaper tab and prevent removal of the indicator device 200. The fastener 212 may pass through the tab 170, such as a pin, rivet or other penetrating fastener. Alternatively, the fastener may only engage the inner 176 and outer 174 surfaces of the tab without penetrating the tab, such as a snap. The fastener may be a separate piece or may be integrally formed with the inner and outer housings. The hinge 206 of the indicator device allows the indicator device to be placed over the tab with the inner housing 204 on the inside of the diaper and the outer housing 202 on the outside. The fastener 212 then secures the indicator device in place.

A hole may be preformed in the tab 170 corresponding to the position of the fastener 212 to aid in proper placement of the indicator device 200.

Figure 9:
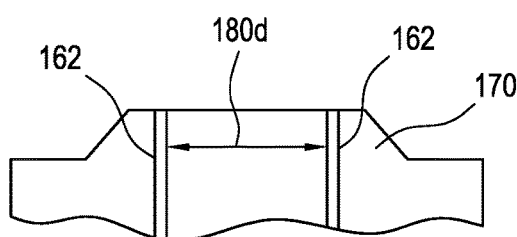
FIG. 9 is a view of spacing between sensor strips of an embodiment of the invention.
Figure 10:
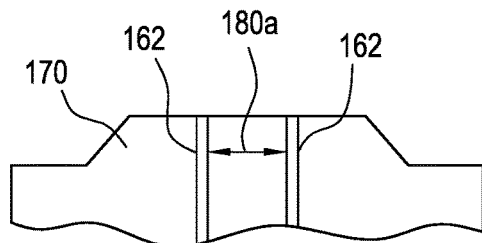
FIG. 10 is a view of alternative spacing between sensor strips of an embodiment of the invention.

FIG. 8 shows the surface 210 of the inside housing 204 that is adjacent to the tab 170. Pins 208 may be formed in spaced pairs 208a, 208b, 208c, 208d. The pin pairs may each consist of single pins or may be made up of groups, clusters or columns of pins. As shown in FIGS. 9-10, the spacing between the strips 162 may vary depending on the size of the diaper. For example, FIG. 9 show an extra large ("XL") diaper with a first strip spacing 180d, while FIG. 10 illustrates a small ("S") diaper with a second strip spacing 180a. This spacing may correspond to the spacing between the pairs of pins 208. For example, spacing 180d of the XL diaper will correspond to the spacing between the outer pair of pins 208d, while the spacing 180a of the S diaper will correspond to the spacing between the inner pair of pins 208a. In this manner, the sensor system will be able to distinguish the size of diaper depending which pair of pins 208 contacts the strips 162.

FIG. 7 shows a front face 216 of the outer housing 202. The housing may include a first indicator light 220. The light may illuminate to indicate that the indicator device has been properly attached to the diaper and the pins 208 have made contact with the strips 162. The indicator device 200 may also emit an audible acknowledgment indicator (a "beep") to indicate that the indicator device has been properly attached. The indicator device 200 may also emit a second audible indicator, different from the acknowledgment indicator, to indicate that the indicator device has not been properly attached. The outer housing 202 may also include a number of indicator lights 218a-d. The indicator lights may correspond and including indicia indicating small, medium, large or extra-large diaper sizes. For example, if the indicator device 200 is attached to the diaper shown in FIG. 9, the pin pair 208d will make contact with the strips 162 spaced apart by distance 180d. The corresponding indicator light 218d on the outer housing 202 will illuminate, indicating that the indicator device has been applied to an extra-large diaper. Alternatively, if the indicator device 200 is attached to the diaper shown in FIG. 10, the pin pair 208a will make contact with the strips 162 spaced apart by distance 180a. The corresponding indicator light 218a on the outer housing 202 will illuminate, indicating that the indicator device has been applied to a small diaper. As illustrated, the indicator device covers a range sizes including S, M, L and XL. However, those skilled in the art will recognize that the indicator lights may correspond and include a narrower or wider range of sizes and size combinations. For example, the indicator device may include additional pins 208 and indicator lights 218 corresponding to additional adult sizes XXL, XXXL, bariatric sizes or various child sizes.

The indicator lights 218 may illuminate automatically upon attachment of the indicator device 200. Alternatively, the front face 216 of the outer housing 202 may include a button 222 or other actuator means to actuate the lights 218. The button 222 may also be configured so that actuating the button allows the caregiver to cycle through the different available sizes with the appropriate light activating when the cycle reaches the size to which the indicator device has been attached. In further embodiments, the outer housing 202 of the indicator device may include a switch, such as a toggle switch, that moves a pair of pins to the spacing that corresponds with the spacing of the desire brief size. In this manner, the pins 208 will only connect to strips 162 and illuminate indicator lights 218, 220 if the indicator device is placed on a diaper of the desired size.

Upon attachment to the diaper, the indicator device may also transmit information regarding the diaper size to a remote display device. The remote display device may be a software application ("app") running on a mobile electronic device, such as a mobile phone or similar. The app may display the size of diaper to which the indicator device has been attached. The app may also compare the size of diaper to which the indicator device has been attached with data entered regarding the intended size for the patient and thereby verify that the size of diaper that has been put on the patient is the size of diaper that should have been used for the patient. The app may include a visual or audible acknowledgement to indicate the correct diaper size has been used.

Figure 11:
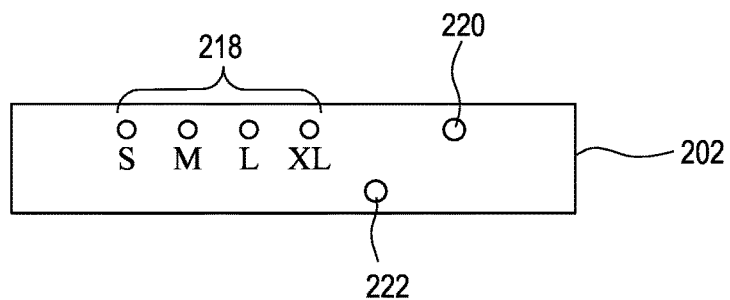
FIG. 11 is a view of a front surface of an outer housing of a further embodiment of the indicator device depicted in FIG. 6.

The indicator device 200 may be sized and configured as appropriate for its function and the comfort of the patient. For example, the outer housing 202 may be generally square shaped as shown in FIG. 7. Alternatively, the housing 202 may be made significantly wider than it is long, as shown in FIG. 11, or longer than it is wide. The housings 202, 204 may also include padding or cushioning to reduce discomfort or ulcer causing pressure points. In FIGS. 6-8 and 11, the housings 202, 204 are illustrated as rigid housings having significant thickness. However, one or both of the housings may be formed with only sufficient thickness to include the necessary elements. The housings may consist simply of printed circuit boards without any enclosing structure. The housings may also be flexible. For example, if pins 208 are made to extend from the outer housing 202, the inner housing 204 may consist only of a flexible piece with sufficient thickness to accommodate the desired fastener 212.

The indicator device 200 may also comprise a magnetically actuated activation and/or locking mechanism. In such a mechanism, a magnetic element is swiped across the outer housing 202 of the indicator device. The magnetic swipe activates the device and moves an internal mechanical locking mechanism that engages and locks fastener 212, thereby preventing the patient from removing the sensor from the diaper.

Figure 12:
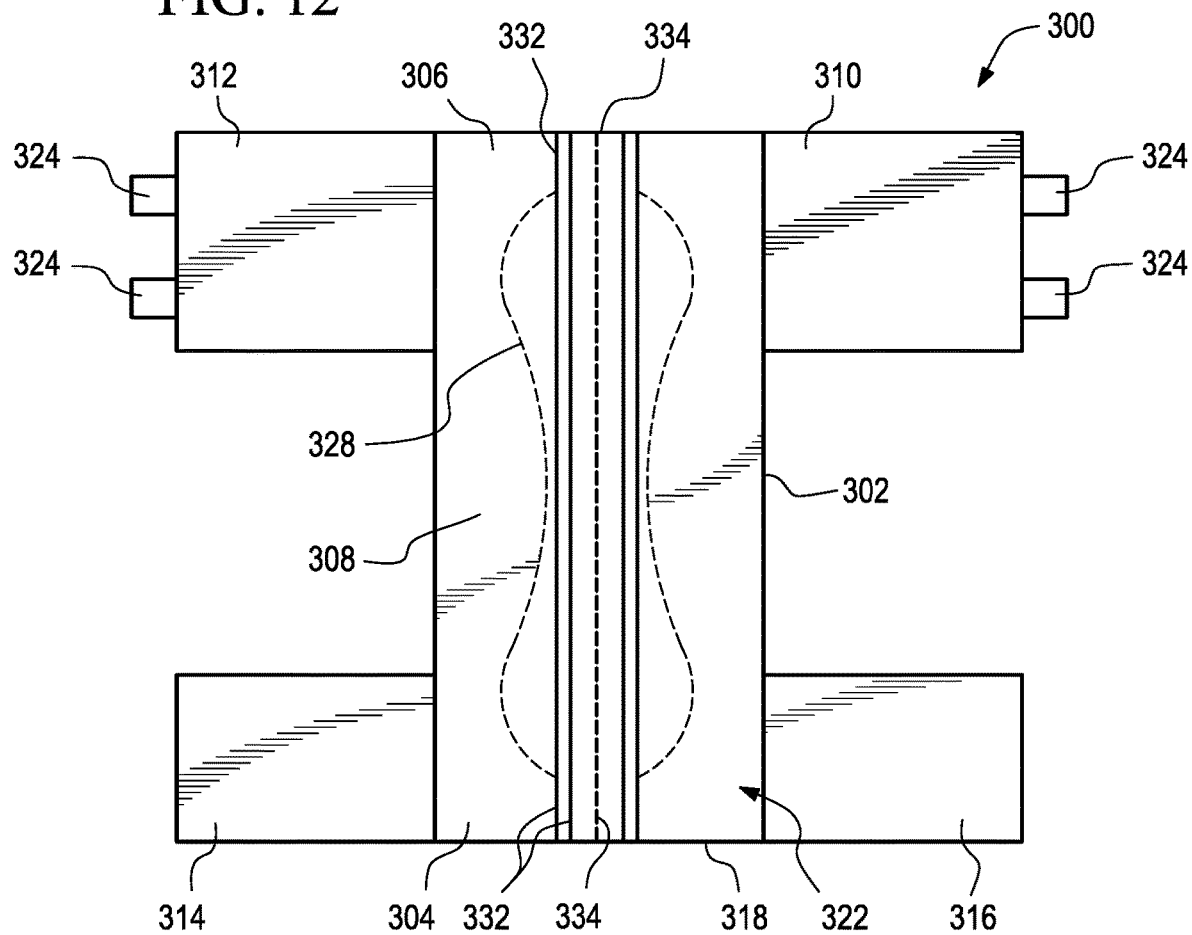
FIG. 12 is a top plan view of an absorbent article with conductive ink and a wetness indicator in a substantially flat un-contracted position according to one embodiment of the invention.

FIG. 12 illustrates an alternative embodiment of the absorbent article 300. In FIG. 12, absorbent article 300 is in a substantially flat un-contracted state. The absorbent article 300 generally consists of several layers, including an inner layer, an absorbent layer, and an outer layer. The inner layer faces a wearer and contacts the skin of the wearer when the absorbent article 300 is secured to the wearer. The plan view of FIG. 12 is shown from the top or patient contacting side of the absorbent article. The topsheet and other components have been removed for clarity. The inner layer may comprise a topsheet that is composed of a moisture-pervious/hydrophilic fabric suitable to allow bodily discharge to pass through the inner layer and be absorbed by the absorbent layer. Non-limiting examples of materials suitable to form the topsheet include polypropylene, polyethylene, polyester, materials having hydrophobic properties, combinations thereof and/or the like. Additionally, the topsheet can be treated with a hydrophilic finish to improve pass through of liquids to diaper layers beneath the inner layer. Non-limiting examples of suitable hydrophilic finishes include stearic acid, melamine-based chemicals, fluorocarbon chemicals, and silicon based chemicals.

As illustrated in FIG. 12, an embodiment of the absorbent article 300 comprises a chassis 302. The chassis 302 includes a front waist region 304, a back waist region 306, and a crotch region 308 that is disposed longitudinally between the front and back waist regions 304 and 306. The front waist region 304 and the back waist region 306 generally comprise those portions of the absorbent article 300 which, when worn, encircle the waist of the wearer. The crotch region 308 is that portion of the absorbent article 300 which, when the absorbent article 300 is worn, is generally positioned between the legs of the wearer.

The chassis 302 has a shape such that its outer perimeter is rectangular or at least substantially rectangular in the illustrative embodiment of the absorbent article 300. In an alternate embodiment, there may be portions of the chassis that are shaped and/or removed, such as in the crotch region 308, for example, resulting in a narrower crotch region portion 308 to provide a contoured fit between the legs. Still other embodiments have different shaped chassis, such as hourglass shapes, T-shapes, and the like.

Rear side panels 310, 312 are coupled to and may extend from the back waist region 306. The disposable article may further include front side panels 314, 316 that are coupled to and may extend from the front waist region 304. The back region 306 is generally positioned against the back of the user. The front region 304 is generally positioned against the front of the user. The rear side panels 310, 312 are configured to wrap around a wearer's waist from back to front, extending from each side of the back waist region 306. The front side panels 314, 316 are configured to wrap around a wearer's waist from front to back. In this manner, rear side panel 312 can be connected to front side panel 314 and rear side panel 310 can be connected to front side panel 316 to couple the front region 304 to the back region 306. In this embodiment there are four side panels 310, 312, 314, 316. However, it should be recognized that other embodiments may be configured with more or fewer side panels. In particular, rear side panels 310, 312 may connect directly to an outside surface of front waist region 304 rather than to front side panels 314, 316.

The side panels may attach to the chassis 302 in a variety of manners as would be apparent to one of skill in the art. Alternatively, one or more of the side panels may be integrally formed, in whole or in part, with a backsheet 318 or topsheet of the absorbent article. The backsheet 318 will have an outside surface 320 (not shown in FIG. 12) facing away from the patient wearing the absorbent article and an inside surface 322 facing toward the patient.

The rear side panels 310, 312 may also include fasteners 324. Fasteners 324 may comprise adhesive tape, hook and loop, snaps or any other appropriate fasteners as would be understood by one of ordinary skill in the art. As shown in the illustrative embodiment, rear side panel 310, 312 includes two fasteners 324. In a preferred embodiment, fasteners 324 can be configured to operatively couple rear side panels 310, 312 to a front region 304 of the diaper chassis 302. Alternative, fasteners 324 may also engage front side panels 314, 316 to attach rear side panels 310, 312, respectively. While FIG. 12 depicts rear side panels 310, 312 as including two fasteners 324, in some embodiments, more or fewer fasteners may be used. While FIG. 12 depicts fasteners 324 sized and shaped a particular way, in other embodiments, fasteners 324 can be a different size and/or shape. Alternatively, the front side panels 314, 316 may include fasteners in addition to, or in place of, the fasteners 324 attached to rear side panels 310, 312.

In another embodiment, the front region 304 and/or front panels 314, 316 may include added or modified features to reinforce or increase the affinity to the fastening device. Additionally, features may be employed to allow adhesive fasteners to be attached and detached from the fastening region multiple times. Those skilled in the art will recognize that there are multiple approaches to doing so via modification of the base material as well as additions of various materials. For example, fasteners 324 may incorporate the hook component of a hook-and-loop closure and portions of the front region 304 and/or front panels 314, 316 may comprise a corresponding loop component. The surface of front region 304 and/or front panels 314, 316 may be treated to increase or decrease the affinity for the hook components. Alternatively, separate loop component material may be adhered to the surface of the front region 304 and/or front panels 314, 316.

An absorbent layer may comprise a first absorbent core 328 and a second absorbent core 330 (not shown in FIG. 12). Embodiments of the absorbent article 300 may further comprise conductive ink 332 printed on the absorbent article 300 for use with a wetness detection system as discussed elsewhere herein. Additional embodiments may comprise a wetness indicator 334 that functions independently or in conjunction with the conductive ink 332. Both the conductive ink 332 and the wetness indicator 334 are coupled to the chassis 302 of the absorbent article 300 that makes contact with the wearer. The conductive ink 332 and wetness indicator 334 may be applied by printing the ink directly on an inside surface 332 of the backsheet 318.

The conductive ink 332 can be applied to the crotch region 308 to leave a space for the wetness indicator 334 to be applied so that it does not interfere or interact with the conductive ink 332, allowing the wetness indicator 334 to be clearly visible on the absorbent article 300. The location of the conductive ink 332 and the wetness indicator 334 can vary when coupled to the absorbent article 300 and can be a variety of patterns, such as solid lines and dashed lines. However, in one embodiment, as shown in FIG. 12, the absorbent article 300 is printed with the conductive ink 332 comprising four lines with two sets of two lines separated by a gap, with the wetness indicator line 334 positioned in the gap. In embodiments of the article, the gap may be between 10 and 20 mm, or more preferably, the gap may be 15 mm.

The conductive ink 332 may function in place of the contact strips 162 (as shown, e.g., in FIGS. 9-10 and discussed above) and likewise may be positioned placed adjacent a top surface 332 of the backsheet 318 below the absorbent core 328. The conductive ink 332 may be printed in a generally strip shape or configuration and may engage an indicator device 200 as describe herein (see, e.g., FIGS. 6-8).

When fluids or human body discharge insults the absorbent article 300, the wetness indicator 334 working in tandem with the conductive ink 332, or working independently, can notify a caregiver of the status of the absorbent article 300. Further, the conductive ink 332, independent of the wetness indicator 334, can notify a caregiver of the status of the absorbent article 300. In one embodiment, the caregiver may use a software application ("app") on a mobile device to know the status of the absorbent article 300. The app may display the size of diaper to which the sensor has been attached. The app may include a visual or audible acknowledgement to indicate the correct diaper size has been used. Furthermore, the app may indicate the time the absorbent article was placed on the wearer and dictate typical absorbent article changing patterns to assist a caregiver. In an alternate embodiment, the conductive ink may communicate with a computing device other than a mobile device.

If the conductive ink 332, indicator device 200, or other aspects of the sensor system do not function properly and the sensor does not indicate a level of wetness, the wetness indicator 334 can be visually checked by the caregiver to determine the status of the absorbent article 300. The wetness indicator 334 is important for a caregiver when the communication between the conductive ink 332 and the receiving device fails or is unavailable. There are many situations that the conductive ink 332 may not be able to communicate its message, for example an internet service disruption, a power outage, or a wearer is outside of the effective range of the receiving device. The wetness indicator 334 allows a caregiver to check the status of an absorbent article 300 in these and other situations. In addition, the wetness indicator may be, but is not limited to, a moisture-sensitive adhesive strip that changes color, disappears, or appears when it is contacted by fluid.

It should be appreciated that any absorbent article may comprise conductive ink 332 and a wetness indicator 334, including but not limited to, incontinence briefs, pads, diapers, etc. for children, adults, or the elderly. It will also be appreciated that other absorbent articles, such as bedding and wound dressings may include a wetness indicator 334 and conductive ink 332. The wetness indicator 334 can act as a fail-safe for any absorbent article known in the prior art. Accordingly, there is a need for a wetness indicator 334 acting as a fail-safe method to visually check the absorbent article 300 in case of failure of the wetness detection system. The present disclosure seeks to solve these and other problems.

Figure 13:
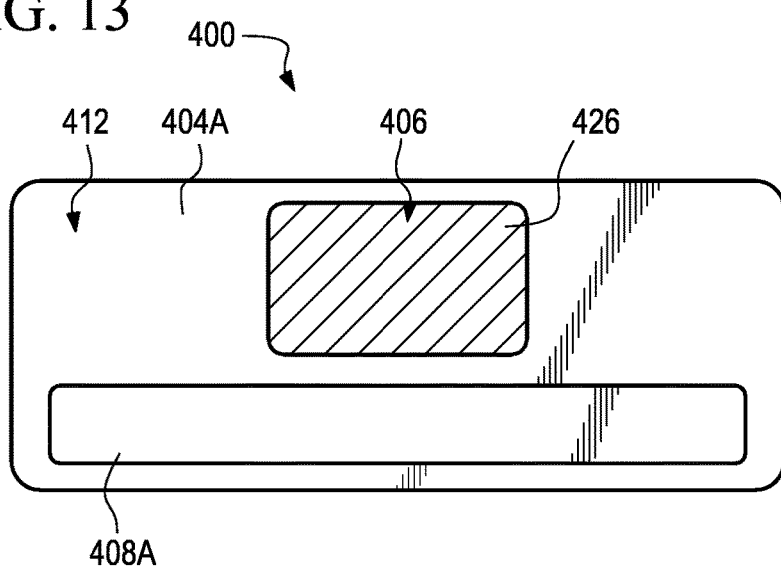
FIG. 13 is a plan view of an inner surface of indicator device with a magnetic securement mechanism and a conductive plate.

In additional embodiments, an indicator device 400 is used for connection with an absorbent article 402. The indicator device 400 comprises a separable housing with two sides 404A, 404B, a securement mechanism 406, one or more conductive plates 408A, 408B, and a transmitter. Alternatively, conductive plates 408A, 408B may comprises other types of electrical or electro-magnetic conductors, couplers or connectors, including, without limitation, pins, metal strips, printed circuits, conductive ink, or the like. As shown in FIGS. 13-14, the housing 404 has a first inner surface 412 on the first housing side 404A and a second inner surface 414 on the second housing side 404B. The housing further comprises a first outer surface 416 and a second outer surface 418. The housing 404 may be in a rectangular shape; however, many other form factors may be used, such as a circle, square, or oval. Each side of the housing 404 may be resistant to or sealed against fluid or other contaminant ingress to enable easy cleaning and to obstruct contamination from penetrating the housing and contacting electrical components within the housing. The housing 404 may be made of a hard material (e.g., metal, plastic).

Further, the securement mechanism 406 may be coupled to the housing 404 on the first and second inner surfaces 412, 414 with some securement mechanisms going through the housing 404 and being positioned on the first and second outer surfaces 416, 418. For example, a user may place the indicator device 400 on or adjacent to an edge 403 of the absorbent article 402 by placing the first inner surface 412 of the housing on an outer surface of the article 402 and the second inner surface 414 of the housing on an inner surface of the article 402. The securement mechanism 406 on both sides of the housing 404 may bring both sides together and couple them to the absorbent article 402. As shown in FIG. 13, the securement mechanism 406 may be magnets 426 that are positioned in the same location on both the first and second inner surfaces of the housing 412, 414. When the two sides come together, with the backsheet 420 trapped in between, the securement mechanism 406 that comprises the magnets 426 couples the two sides of the housing 404.

Figure 16:
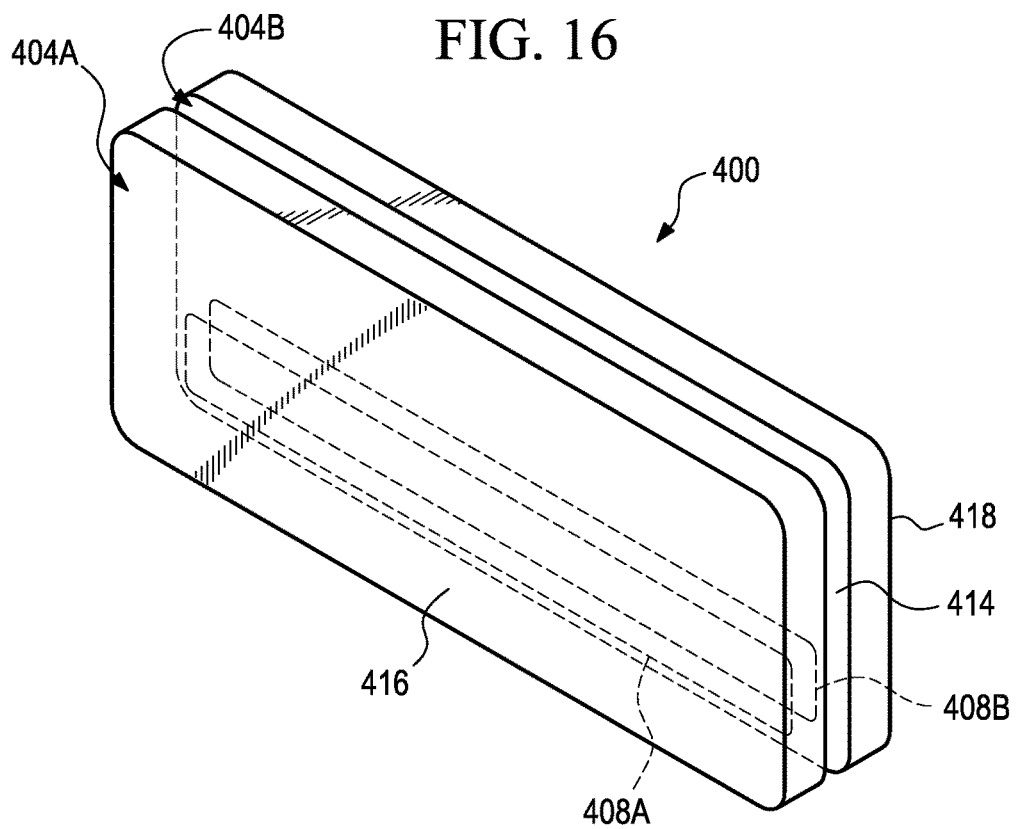
FIG. 16 is a perspective view of an indicator device.
Figure 17:
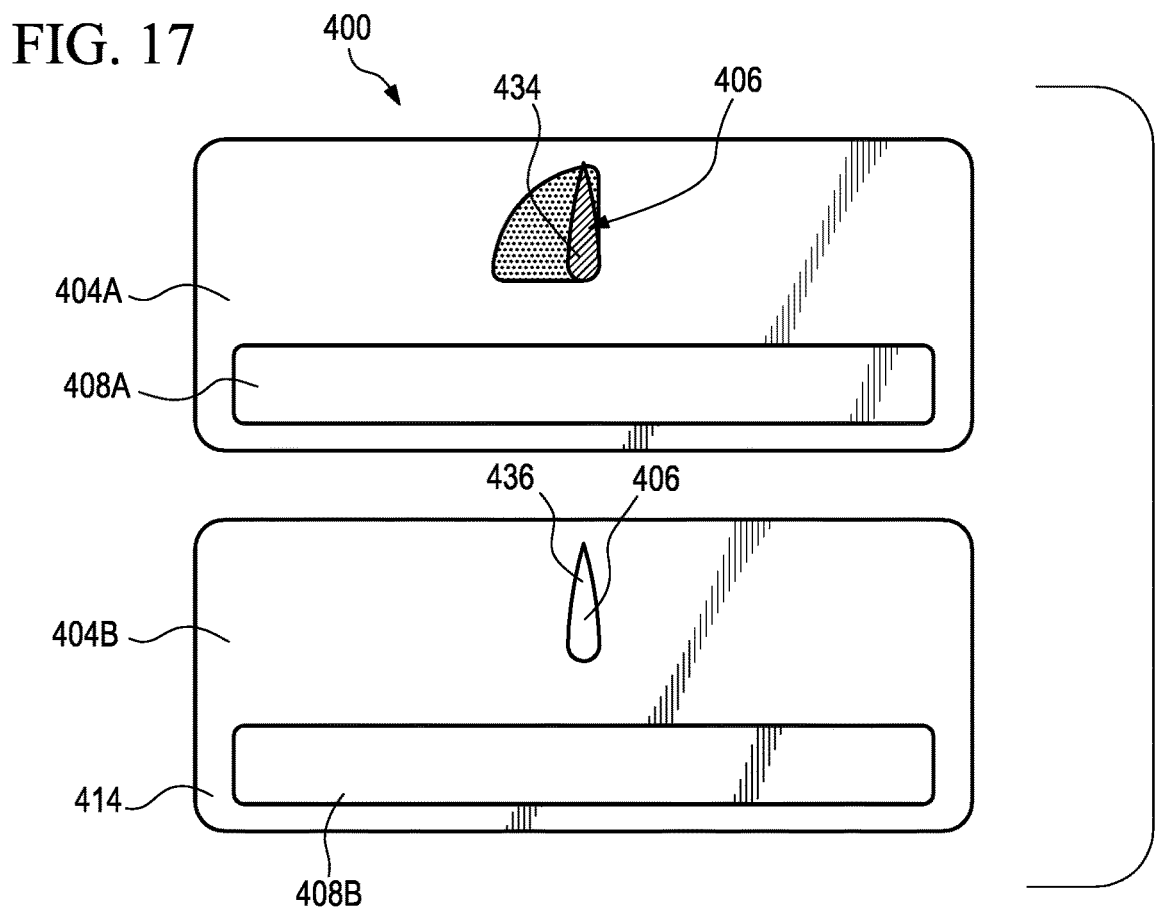
FIG. 17 is a plan view of an indicator device with a winged turn pin securement mechanism and conductive plates.
Figure 18:
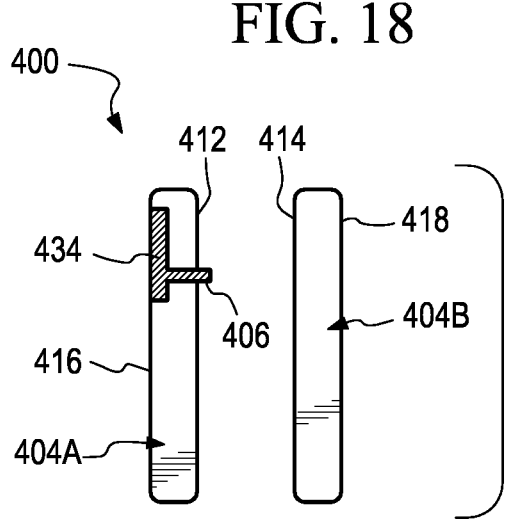
FIG. 18 is a side elevation view of an indicator device with a winged turn pin securement mechanism.
Figure 19:
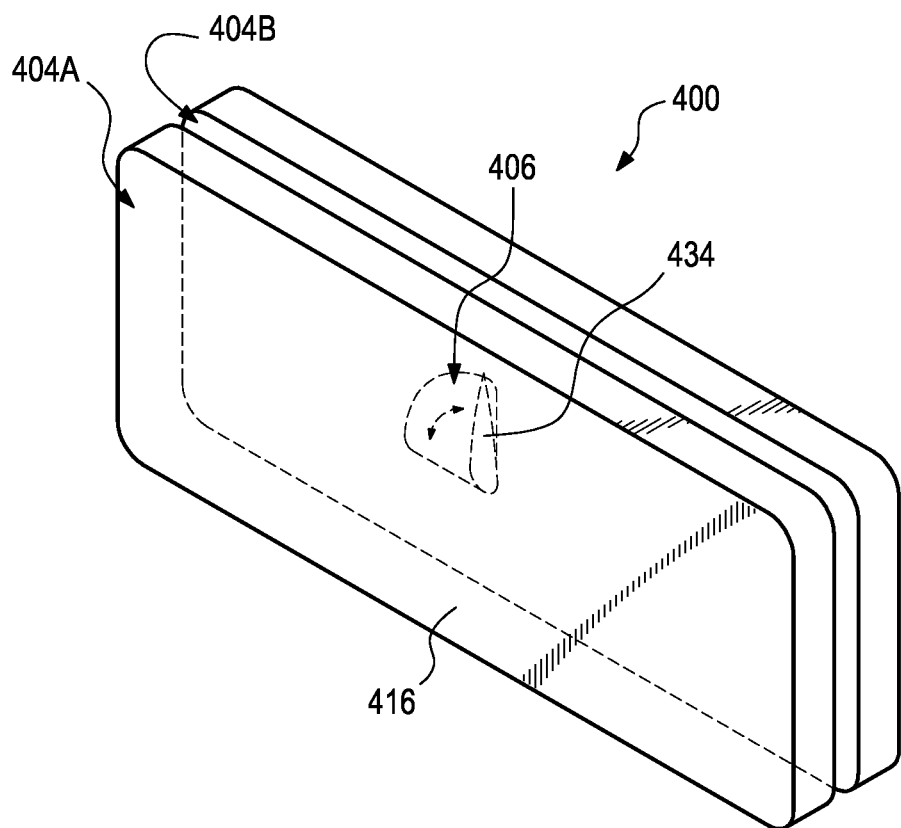
FIG. 19 is a perspective view of an indicator device with a winged turn pin securement mechanism.

Referring to FIGS. 14-16, in some embodiments, the securement mechanism 406 comprises a snap fitting 428. For example, the first inner surface 412 of the housing comprises a male snap feature 430 and the second inner surface 414 of the housing comprises a female receiving snap feature 432. The two sides can couple or snap together through an aperture on the backsheet 420 of the absorbent article 402. In an alternate embodiment, as shown in FIGS. 17-19 a securement mechanism 406 comprises a winged turn pin 434. The first outer surface 416 of the housing comprises the winged turn pin 434 that protrudes through a side of the housing and the first inner surface 412. The second inner surface 414 of the housing 404 comprises a receiving aperture 436. The winged turn pin 434 would be inserted into the receiving aperture 436. When the winged turn pin 434 is in the receiving aperture 436, the winged turn pin 434 is then turned to lock the two sides of the housing 404 together. It should be appreciated that the two sides of the housing 404 can come preassembled onto the absorbent article 402. The indicator device 400 may further comprise a locking feature that works in conjunction with the securement mechanism 406 or separately. The locking feature would prevent a wearer from easily removing the indicator device 400. The locking feature could be a latch that needs to be released before the pod can be removed or a lever that needs to be depressed for the pod to be removed.

A securement mechanism 406 for an indicator device 400 that does not comprise a pin hinge may provide advantages over a securement mechanism that incorporates a pin hinge. For example, a living hinge securement mechanism may provide fewer locations for debris to collect, and therefore fewer locations that can harbor bacteria and can be cleaned easily with a simple disinfectant wipe. Specifically, the living hinge may be used to connect a housing with two sides. Further, the living hinge may be removably attachable to the housing with two sides or may be permanently coupled thereto.

Figure 20:
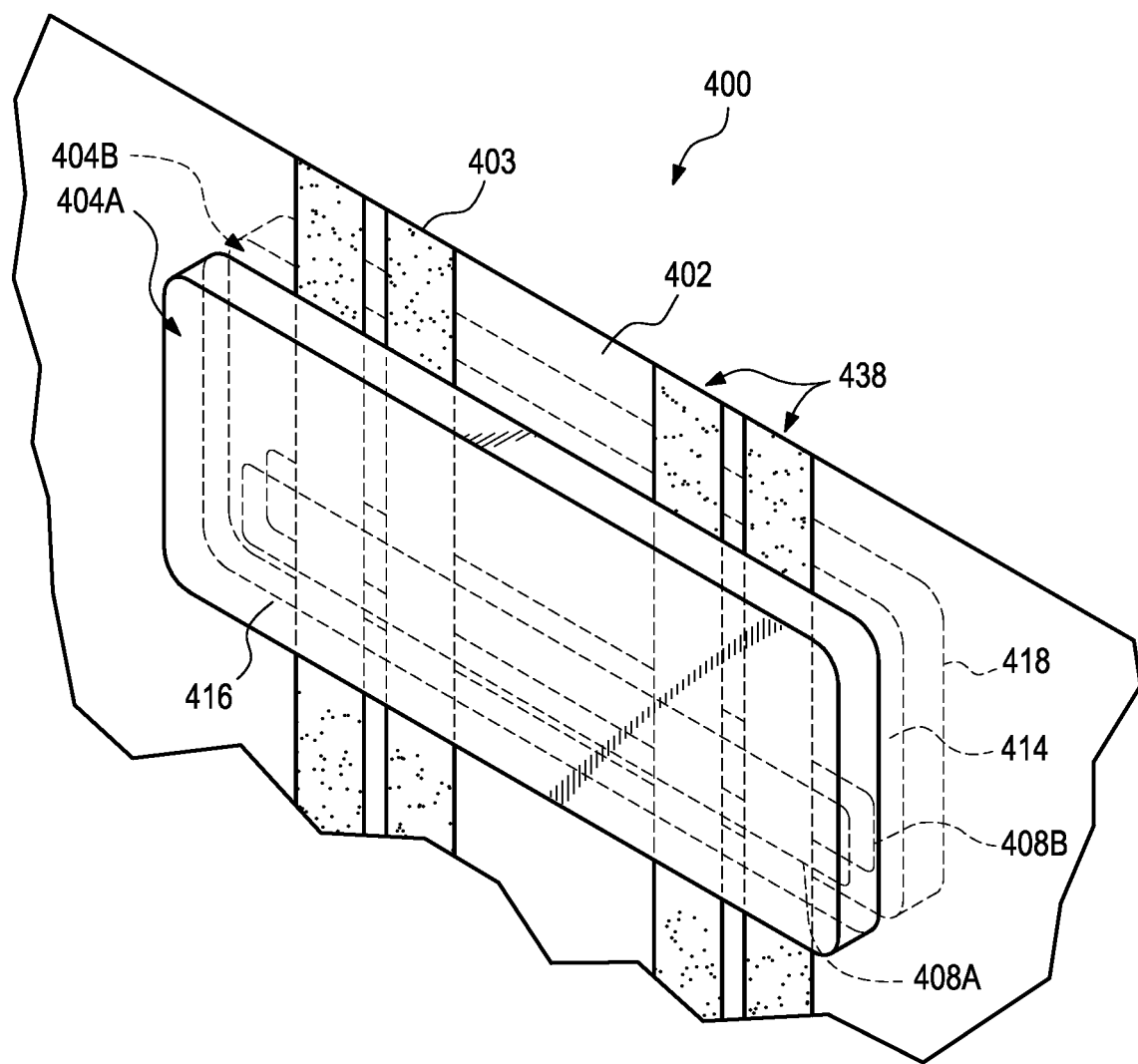
FIG. 20 is a perspective view of an indicator device coupled to an absorbent article.

As illustrated in FIG. 20, in embodiments of the sensor system, the conductive plates 408 communicate with conductive ink lines 438 that are printed on the absorbent article 402. Alternatively, metal strips 162 (FIGS. 9-10) may be used in place of the conductive ink lines. As shown in FIG. 20, the indicator device 400 couples to the absorbent article 402 with the conductive plates 408 connected the printed conductive ink lines 438. The connections between the conductive ink lines 438 and the conductive plates 408 may be made in various different forms as would be known by one of ordinary skill in the art. For example, the ink lines 438 and plates 408 may be in physical contact to allow electric conductivity between the ink lines 438 and plates 408. Alternatively, a top sheet 130 (FIG. 2) may be positioned over the top of the ink lines 438 so that neither of the plates 408A, 408B directly contacts the ink lines 438.

When the absorbent article 402 has been infiltrated with human excrements, the conductive ink 438 communicates with the indicator device 400. The indicator device 400, in particular the transmitter, can then communicate with an electronic device. The transmitter is able to send this information so that the medical care provider knows the status of the absorbent article 402. The conductive plates 408 of the indicator device 400 have a large interfacing surface allowing a clear communication between the ink and the indicator device 400 when a non-contact connection is used. While the preferred absorbent article may be a disposable brief, other absorbent articles may be used with the indicator device 400. For example, the indicator device could be used with, but is not limited to, wound dressings and bedding.

In one embodiment, an indicator device 400 comprises a housing that is made of a soft material, such as a silicone rubber. The housing with a rubber material can also prevent ingress of any fluids. In addition, having a pliable housing may prevent irritation to a wearer's skin. It also provides comfort while the wearer is in prostrate position.

In an additional embodiment, the indicator device 400 comprises a housing that is made of a hard material, such as plastic or metal. In one embodiment, the housing may be made of polypropylene. The housing with the hard material further comprises a soft covering. The soft covering may be a soft plastic, a silicone material, a washable fabric, etc. that can be removably attachable or permanently attached to the housing. A soft outer covering provides a comfortable interface for a wearer that prevents any discomfort that could be found with a non-pliable plastic.

Figure 21:
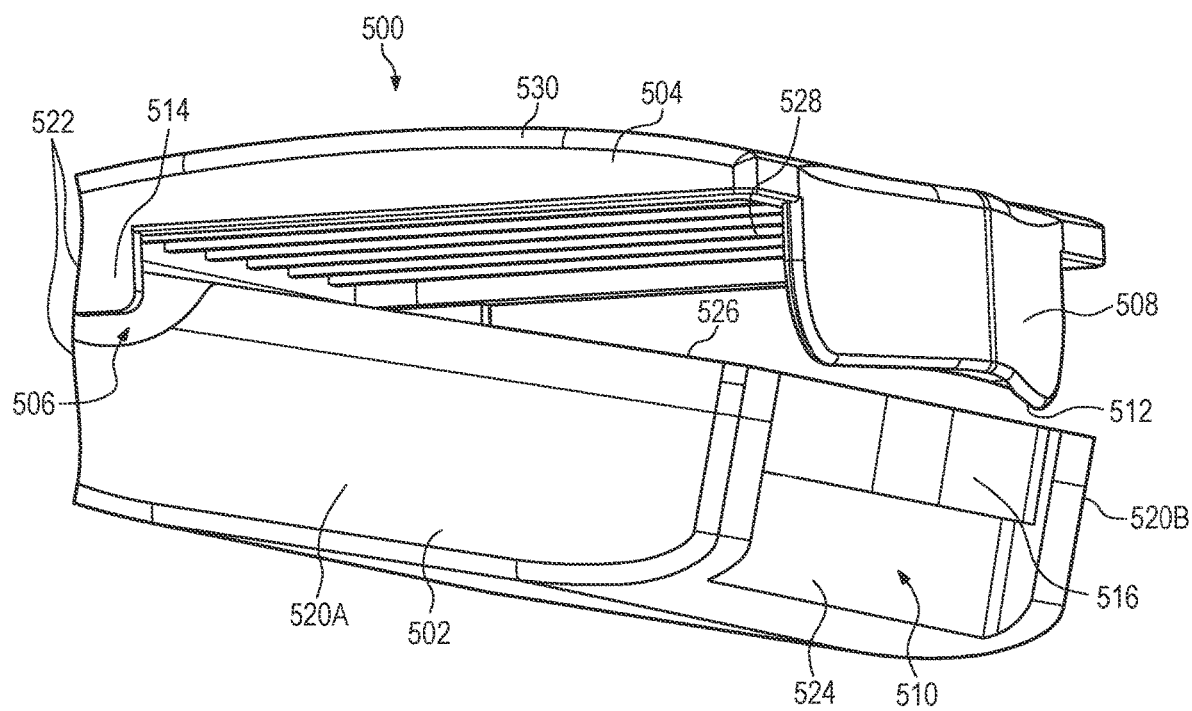
FIG. 21 is a front perspective view of an indicator device with a lid in an open position.

In additional embodiments illustrated in FIGS. 21-27, various indicator device securement mechanisms are illustrated. It will be appreciated that any of these securement mechanisms, or other features mentioned below, may be applied to previously discussed embodiments. Referring to FIG. 21, in one embodiment, an indicator device 500, which is coupleable to an absorbent article (e.g., absorbent article 300), comprises a housing 502 with a lid 504 hingedly coupled thereto, which may seal or unseal the housing 502. The terms lid and housing are used herein only to distinguish portions of a separable housing with two sides. The lid 504 may not contain components and may be narrower than the housing 502. Alternatively, the lid may be thicker than the housing and/or may contain various components.

The housing 502 may comprise a cavity 526 surrounded by the housing front 524, side 520A, 520B and rear 522 walls. The cavity 526 may house one or more electronic components of the indicator device 500, including for example, a battery, electronic circuitry, conductors, contacts, printed circuit boards, or other appropriate elements as discussed herein or understood by one of ordinary skill in the art. Embodiments of the lid 504 may extend over an entire opening of the cavity 526 such that the lid 504 forms a top wall of the cavity 526 when the lid is closed. The lid may have an inside surface 528 and out outside surface 530.

Embodiments of the housing 502 comprises recessed pivot area 506 and a recessed receiver 508 on an outside surface 510 of the front wall 520 of the housing 502. The housing 502 may be in a rectangular shape; however, many other form factors may be used, such as circular, ovular, etc. The housing 502 may be made of a hard material, such as metal, plastic, or any other hard material. In some embodiments, the housing 502 may comprise a grip material, such as silicone raised dots or lines. In one embodiment, the grip material may be manufactured with the housing 502, thereby making a single unit with the grip material. In other words, the grip material may be created via a mold for the housing 502. Accordingly, when the housing is manufactured, the grip material is incorporated into the housing 502 as part of the mold.

The lid 504 may be hingedly coupled to the housing 502 at a first end of the lid and extend along longitudinal lid axis to a second end. The lid may be coupled to the housing via a living hinge, pin hinge, or any other type of hinge. However, it will be appreciated that a living hinge may provide fewer locations for debris to collect, and therefore fewer locations that can harbor bacteria, allowing it to be cleaned easily with, for example, a simple disinfectant wipe. The lid 504 comprises a latch 508 protruding therefrom. The latch may comprise a protrusion 512 that extends from a surface of the latch 508, and which may engage a recess or indentation 516 of the housing 502 via tension or other securement mechanisms. The latch may extend from the lid along a longitudinal latch axis and at an angle such that the longitudinal latch axis is nonparallel to the longitudinal lid axis. The recess 516 may be formed in the housing front wall 524, and the latch may also cover a portion of the outside surface of the housing front wall 524. Embodiments of the latch 508 may extend along a distance that is greater than 50% of the length of the front wall 524. Alternatively, latch 508 may extend along a distance that is greater than 75% of the length of the front wall 524.

The housing 502 may be made resistant to the intrusion of fluids or other foreign materials such as dust or lint when the lid 504 is in a closed and secured position or an opened position, to enable easy cleaning and to prevent any contamination from penetrating the housing 502 and contacting electrical components within the housing 502. In particular, the internal electrical components are sealed so as to allow cleaning of contaminants and to prevent intrusion of fluids. Accordingly, the housing 502, whether in an opened or closed position, may be sealed or made impervious against any fluid ingress.

The lid 504 further comprises side protrusions 514 positionable in the recessed pivot area 506. The side protrusions 514 may prevent the absorbent article from being inserted too far into the housing 502 and interfering with the hinge and/or closure mechanism. The side protrusions 514 may also assist and guide a user to position the housing 502 at a correct depth, which may be when the absorbent article contacts the side protrusions 514. To open the lid 504, a user lifts up on the latch 512, releasing the lid 504 and allowing the side protrusions 514 to pivot in the recessed pivot area 506, thereby allowing a user to remove the housing from the absorbent article and access an inside of the housing 502.

Figure 22:
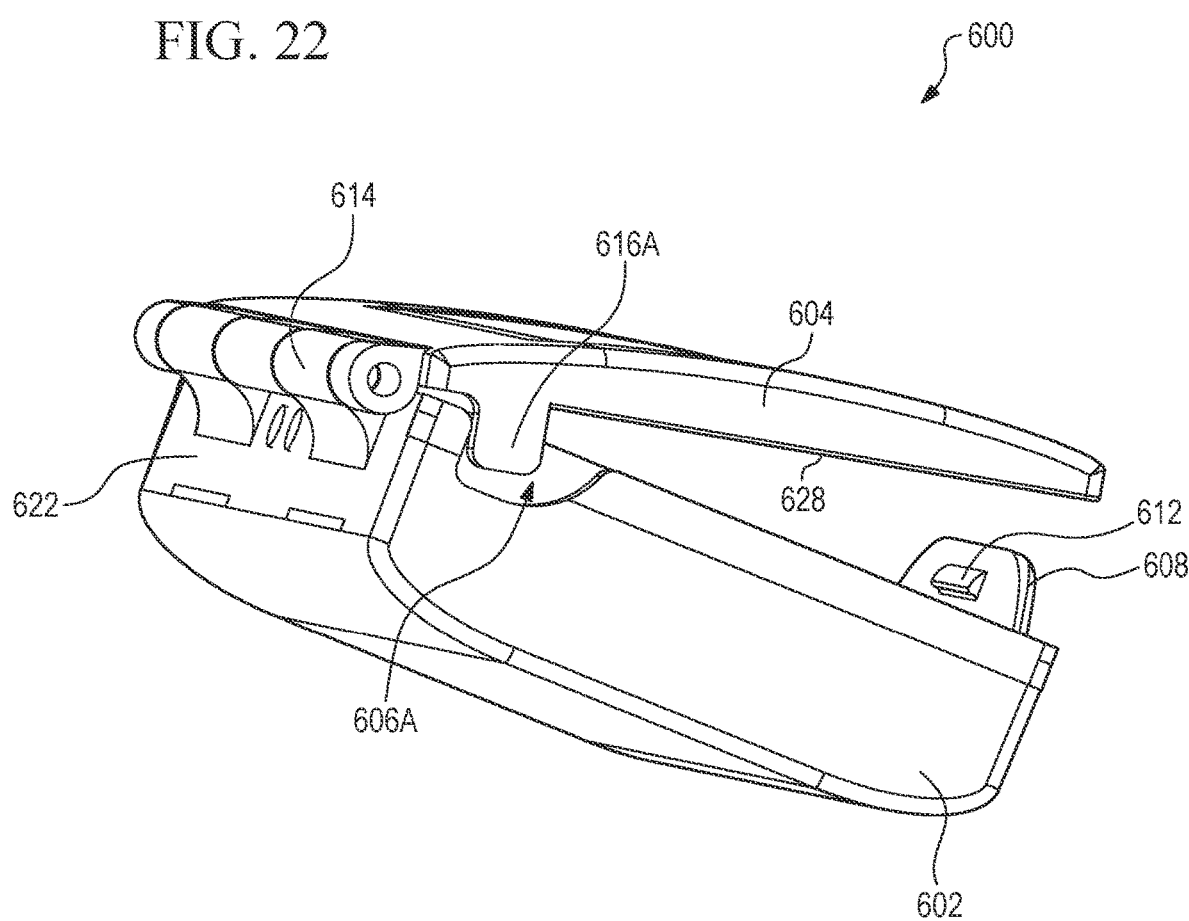
FIG. 22 is a rear, side perspective view of an indicator device with a lid in an open position.
Figure 23:
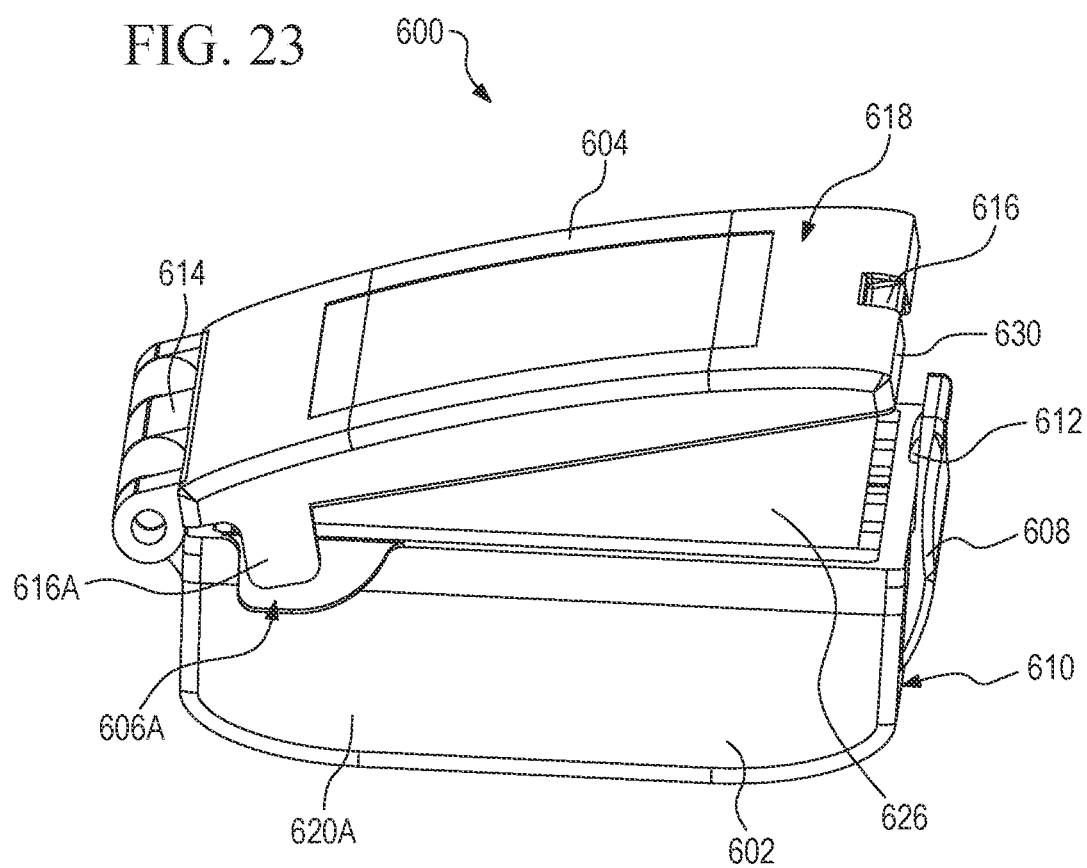
FIG. 23 is a side perspective view of the indicator device of FIG. 22.
Figure 24:
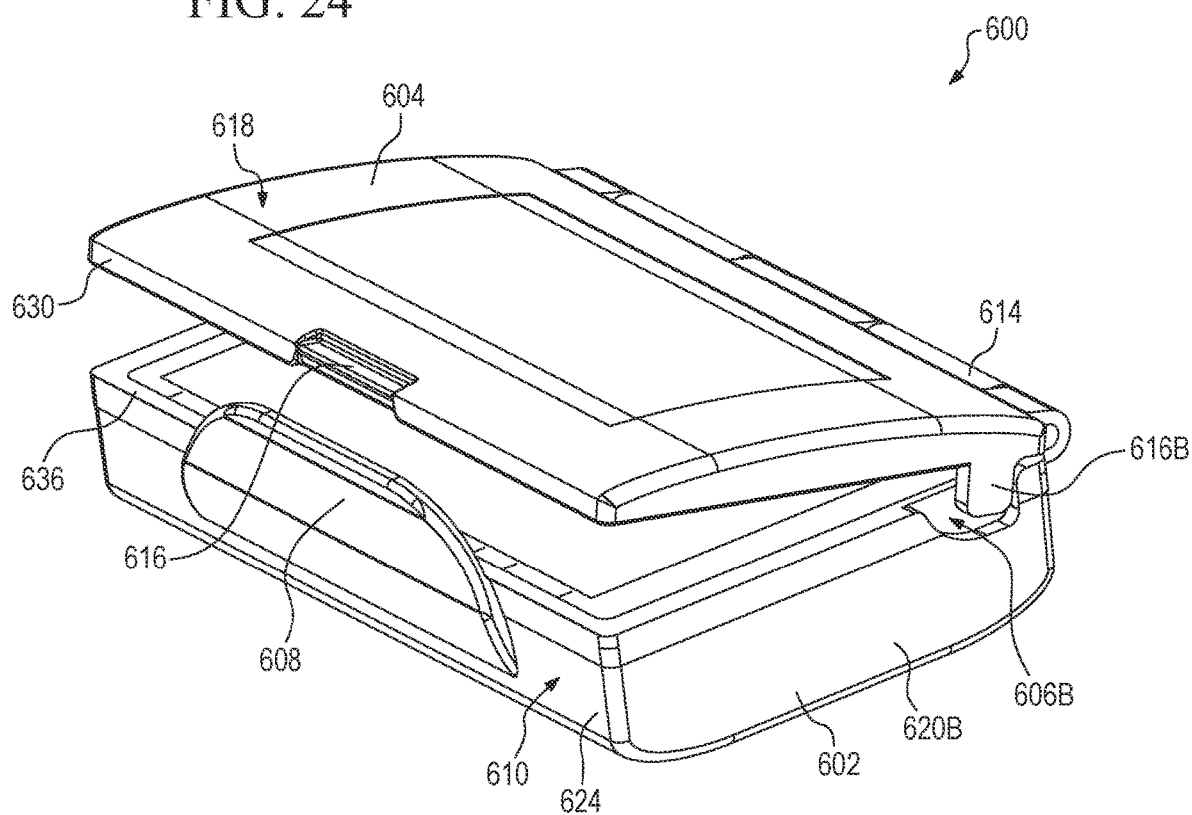
FIG. 24 is a perspective view of the indicator device of FIG. 22.

Referring to FIG. 22-24, in one embodiment, an indicator device 600, which is coupleable to an absorbent article (e.g., absorbent article 300), comprises a housing 602 with a lid 604 hingedly coupled thereto so as to seal or unseal the housing 602. The housing 602 comprises recessed areas 606A, 606B and a latch 608 extending vertically from a front surface 610 of the housing 602. The latch 608 comprises a protrusion 612 so as to receive and secure the lid 604. The housing 602 may be in a rectangular shape or any other form factor, such as circular. The housing 602 may be made of a hard material, such as metal, plastic, or any other hard material. In some embodiments, the housing may be manufactured from a pliable material. As described in the embodiment above, the housing 602 may comprise, in some embodiments, a grip pattern or material to improve the grip of a user when handling the indicator device 600.

The housing 502 may comprise a cavity 626 surrounded by the housing front 624, side 620A, 620B and rear 622 walls. The cavity 626 may house one or more electronic components of the indicator device 600, including for example, a battery, electronic circuitry, conductors, contacts, printed circuit boards, or other appropriate elements as discussed herein or understood by one of ordinary skill in the art. Embodiments of the lid 604 may extend over an entire opening of the cavity 626 such that the lid 604 forms a top wall of the cavity 626 when the lid is closed. The lid may have an inside surface 628 and out outside/top surface 618.

The lid 604 may be hingedly coupled to the housing 602 via a lid hinge 614. While the lid hinge 614 illustrated is a pin hinge, it will be understood that any other type of hinge may be used, such as a living hinge. The lid 604 comprises a receiving indentation 616 that receives the protrusion 612 of the latch 608. The indentation may extend downwardly from a top surface 618 of the lid. The indentation may also extend inwardly from a front edge 630 of the lid. Embodiments of the indentation extend across or parallel to the lid front edge across a distance that is less than the length of the front edge. The indentation 616 may extend across a distance that is less than 50% of the length of the font edge 630. Alternatively, indentation 616 may extend across a distance that is less than 25% of the length of the font edge 630.

With regard to function, as the lid 604 is closed, the receiving indentation 616 contacts the protrusion 612, which places pressure on the latch 608, pushing it away from the housing 602, and allowing the protrusion 612 to slide over and be secured on top of the receiving indentation 616. To open the lid 604, a user pulls the latch 608 away from the housing 602, thereby releasing the protrusion 612 from the receiving indentation 616 and allowing the lid 604 to be in an open position. Additionally, the lid 604 may comprise channel protrusions 616A, 616B positioned in the recessed areas 606A, 606B. As the lid 604 is opened and closed, the channel protrusions 616A, 616B may pivot in the recessed areas 606A, 606B. In some embodiments, the lid 604 may not have channel protrusions. It will be appreciated that the housing 602 may be resistant to or sealed against contaminant ingress to enable easy cleaning and to obstruct contamination from penetrating the housing 602 and contacting electrical components within the housing 602.

Figure 25:
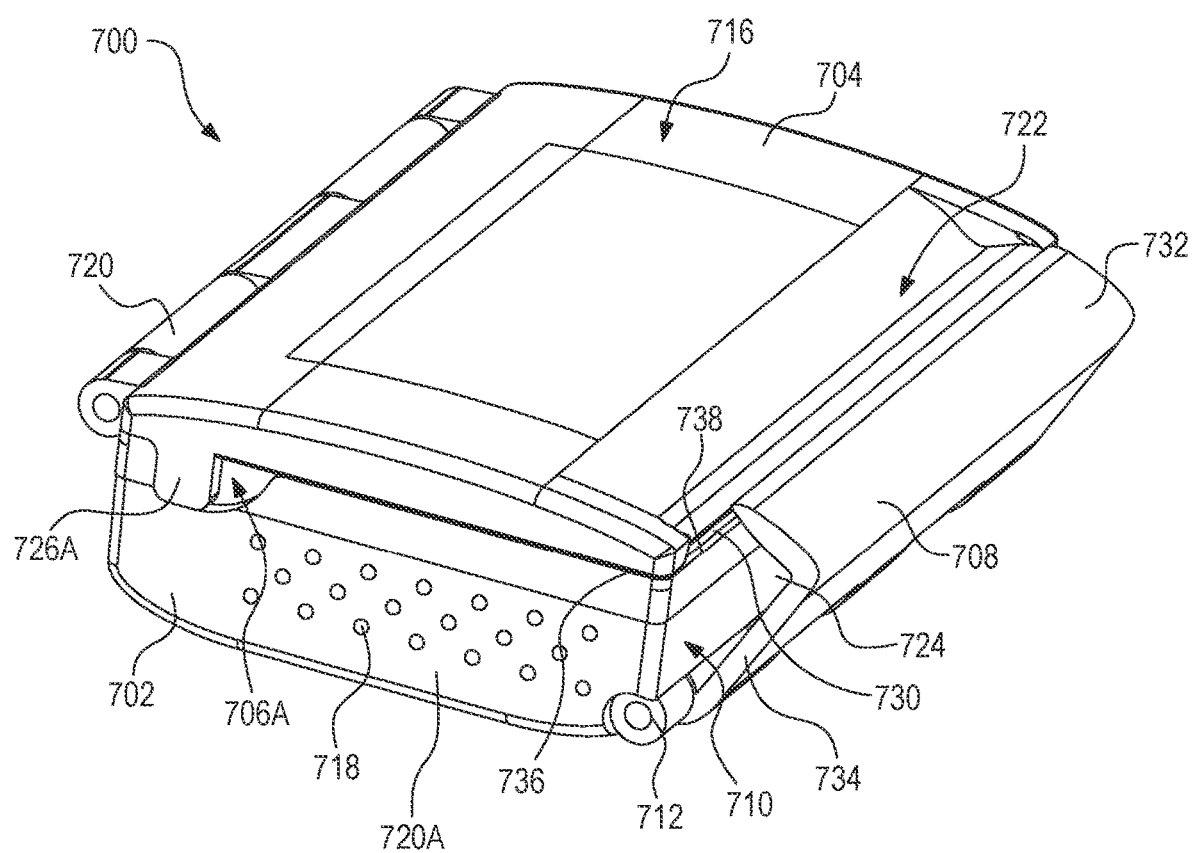
FIG. 25 is a top perspective view of an indicator device.
Figure 26:
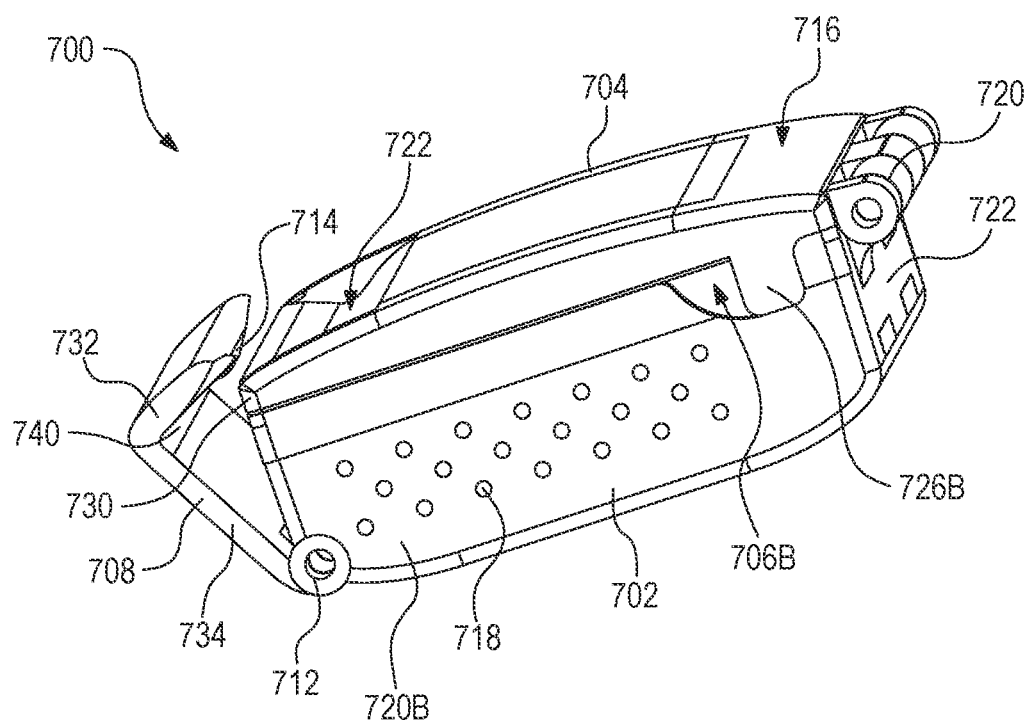
FIG. 26 is a right side perspective view of the indicator device of FIG. 25
Figure 27:
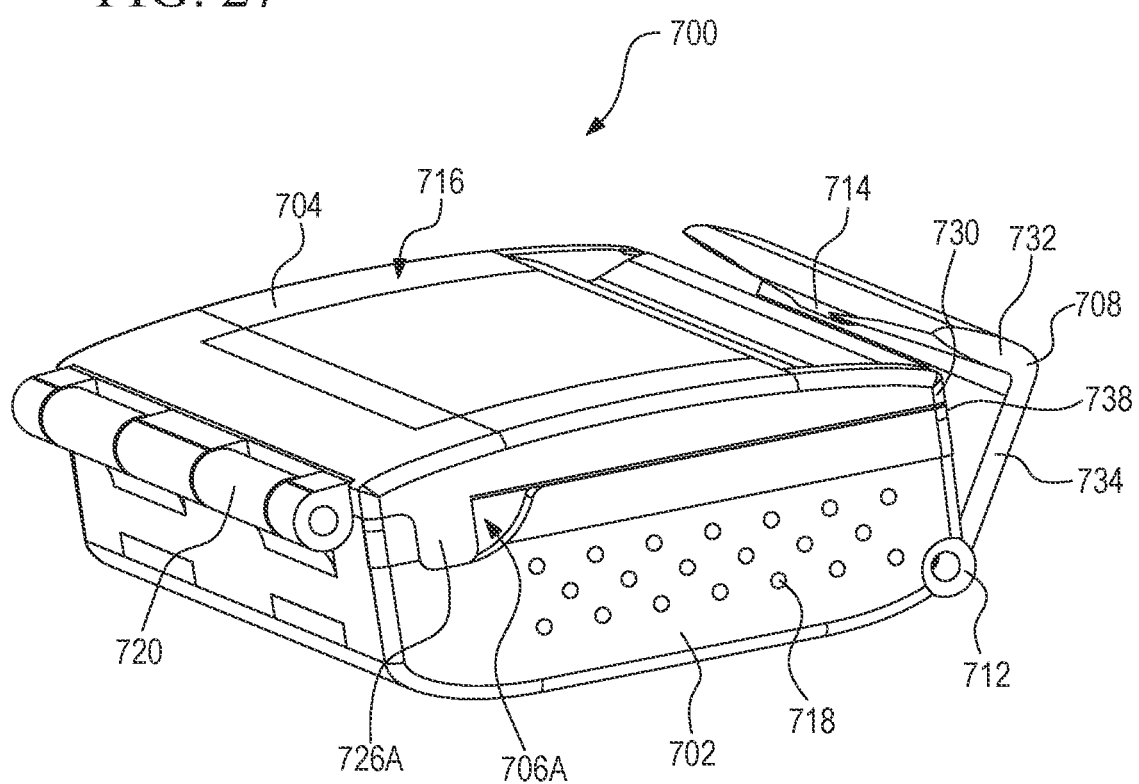
FIG. 27 is a left side perspective view of the indicator device of FIG. 25.
Figure 28:
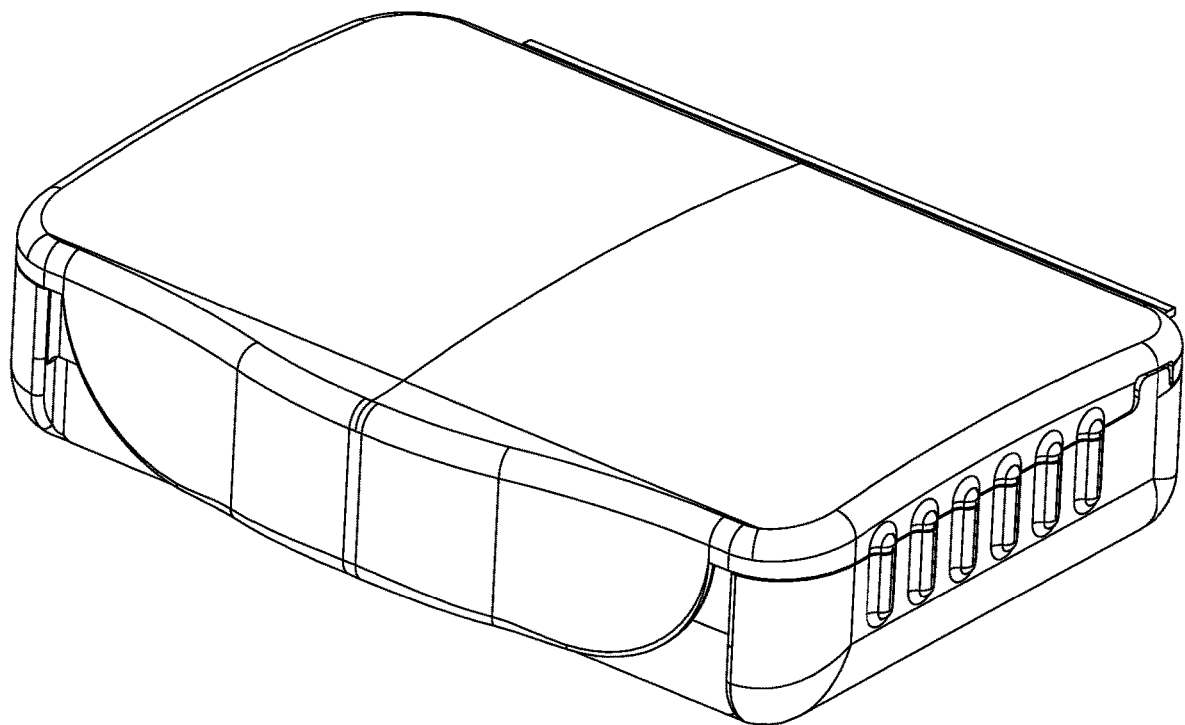
FIG. 28 is a front perspective view of an indicator device.
Figure 29:
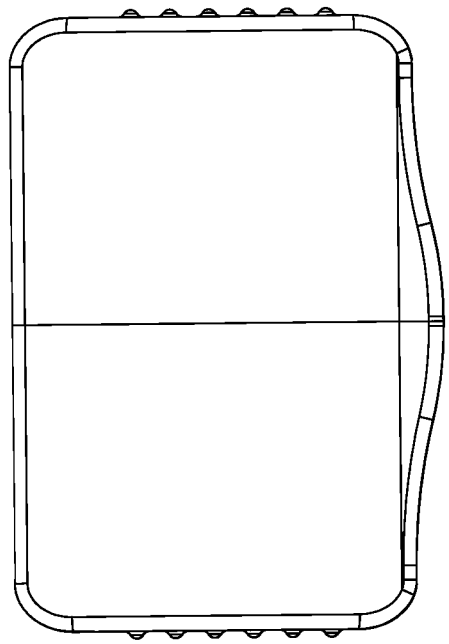
FIG. 29 is a bottom plan view of the indicator device of FIG. 28.
Figure 30:
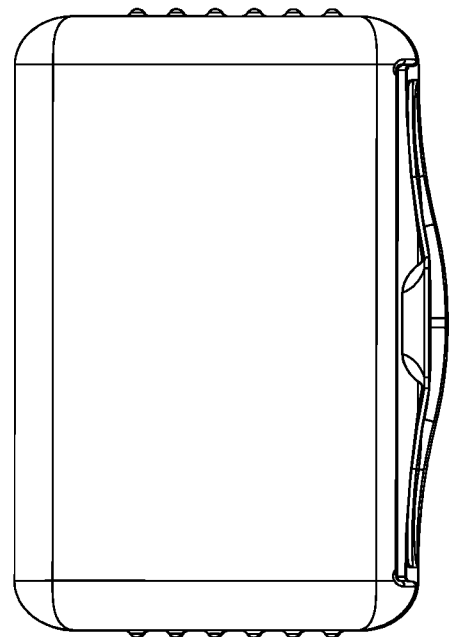
FIG. 30 is a top plan view of the indicator device of FIG. 28.
Figure 31:
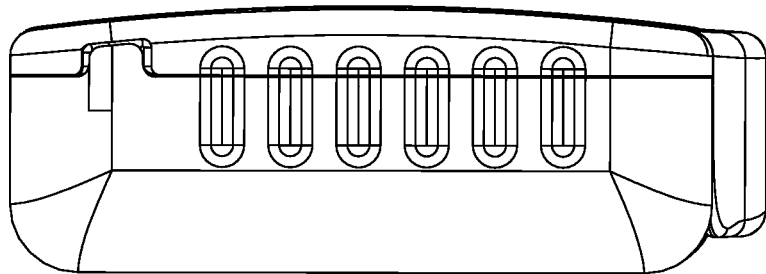
FIG. 31 is a left side elevation view of the indicator device of FIG. 28.
Figure 32:
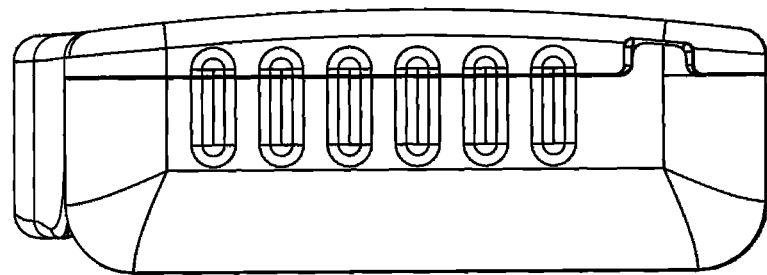
FIG. 32 is a right side elevation view of the indicator device of FIG. 28.
Figure 33:
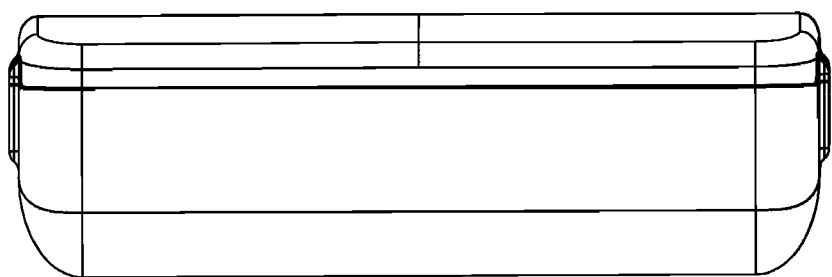
FIG. 33 is a rear elevation view of the indicator device of FIG. 28.
Figure 34:
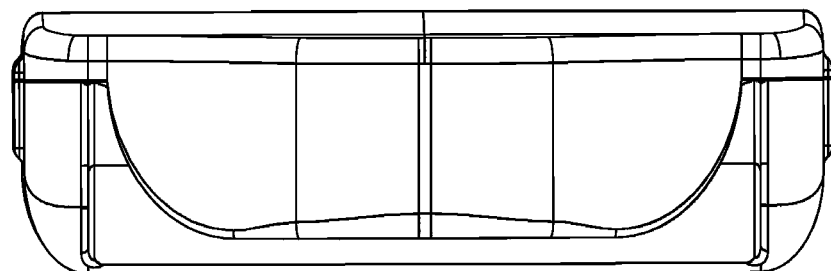
FIG. 34 is a front elevation view of the indicator device of FIG. 28.
Figure 35:
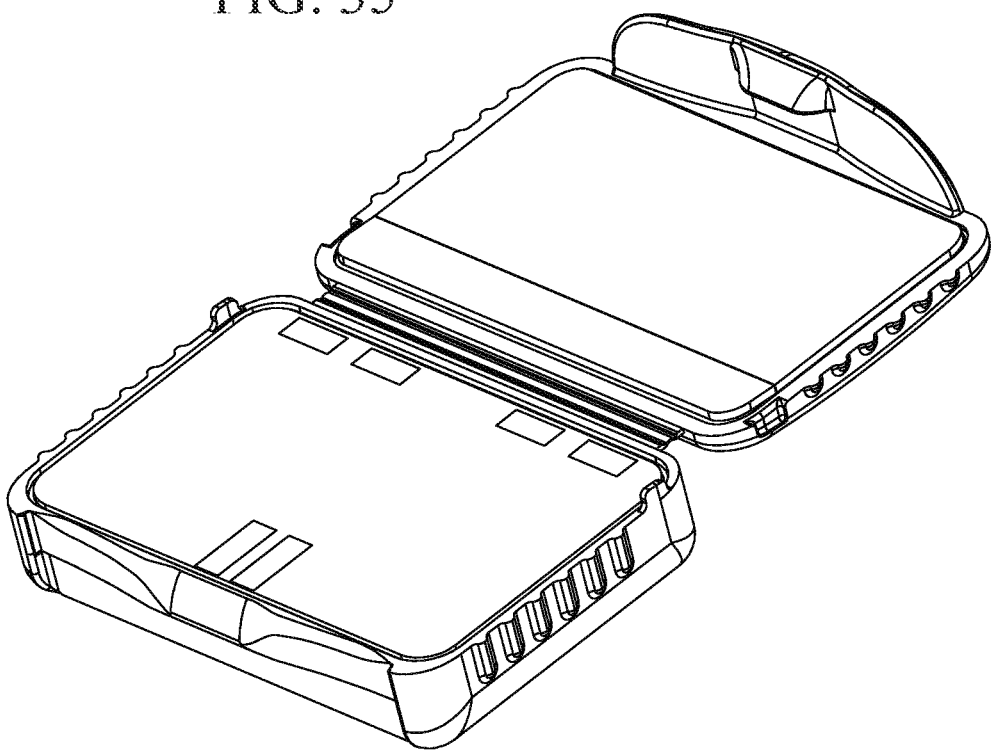
FIG. 35 is a front perspective view of the indicator device of FIG. 28 with a lid in an open position.
Figure 36:
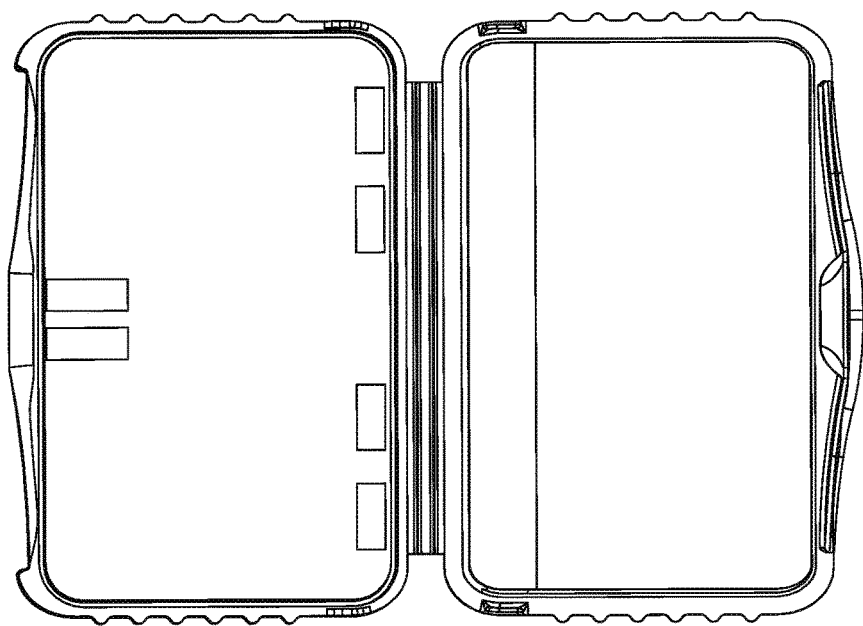
FIG. 36 is a top plan view of the indicator device of FIG. 28 with the lid in an open position.
Figure 37:
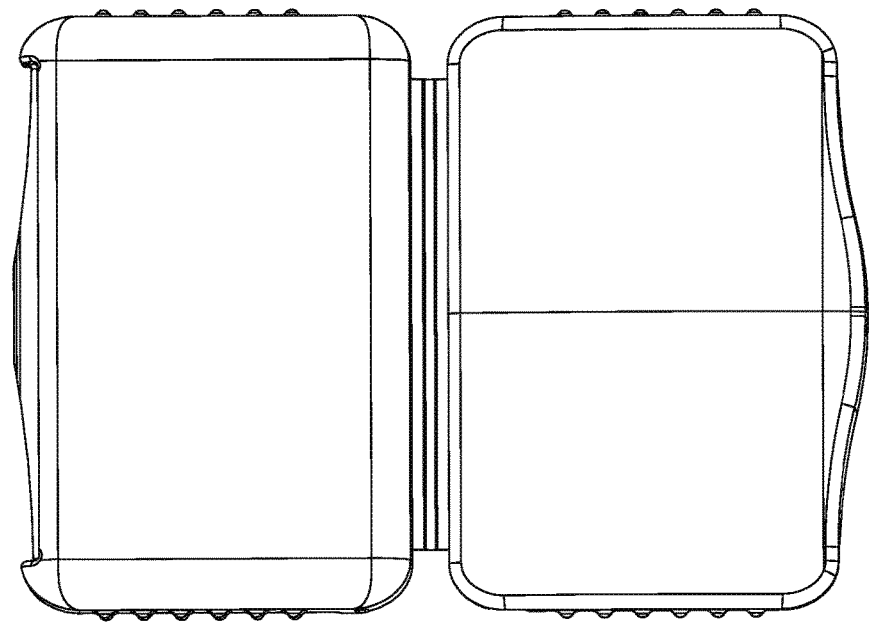
FIG. 37 is a bottom plan view of the indicator device of FIG. 28 with the lid in an open position.
Figure 38:
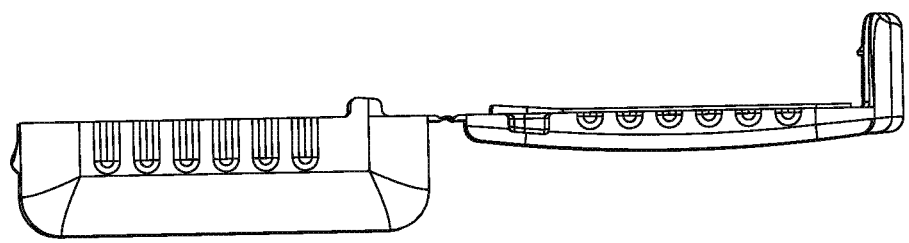
FIG. 38 is a right side elevation view of the indicator device of FIG. 28 with the lid in an open position.
Figure 39:
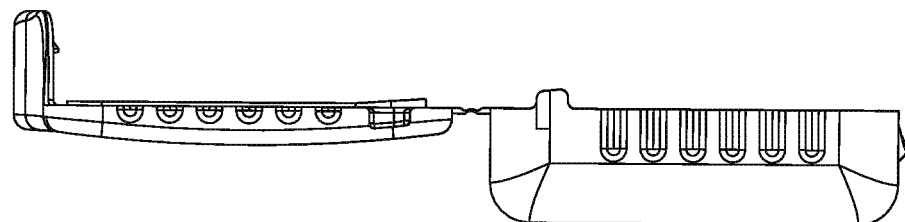
FIG. 39 is a left side elevation view of the indicator device of FIG. 28 with the lid in an open position.
Figure 40:
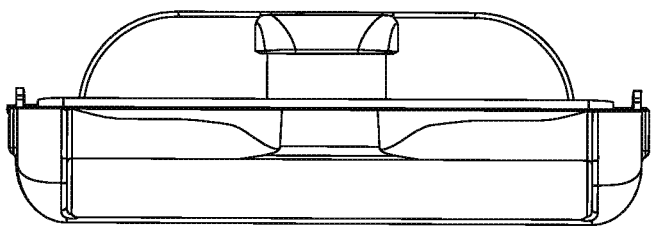
FIG. 40 is a front elevation view of the indicator device of FIG. 28 with the lid in an open position.
Figure 41:
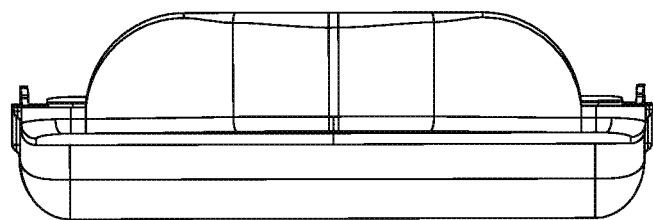
FIG. 41 is a rear elevation view of the indicator device of FIG. 28 with the lid in an open position.

Referring to FIG. 25-27, in further embodiments, an indicator device 700, which is coupleable to an absorbent article (e.g., absorbent article 300), comprises a housing 702 having an outside surface 710 and a lid 704 hingedly coupled thereto so as to close the housing 702. The housing 702 comprises recessed areas 706A, 706B and a latch 708 which may be hingedly coupled to a front surface 710 of the housing 702. The latch 708 may couple to the housing via a latch hinge 712. As illustrated, the latch hinge 712 may be a pin hinge. However, other types of hinges may be used, such as a living hinge.

The housing 702 may comprise a cavity surrounded by the housing front 724, side 720A, 720B and rear 722 walls. The cavity may house one or more electronic components of the indicator device 700, including for example, a battery, electronic circuitry, conductors, contacts, printed circuit boards, or other appropriate elements as discussed herein or understood by one of ordinary skill in the art. Embodiments of the lid 704 may extend over an entire opening of the cavity such that the lid 704 forms a top wall of the cavity when the lid is closed.

Furthermore, the latch 708 may comprise a protrusion 714 that when positioned on an outside surface 716 of the lid 704, secures the lid 704. The housing 702 may be in a rectangular shape or any other shape. The housing 702 may be made of a hard material, such as metal, plastic, or any other hard material. In some embodiments, the housing may be manufactured from a pliable material. Additionally, the housing 702 may comprise a grip texture or material 718, such as raised bumps or silicone grip dots, to assist a user in holding the indicator device 700.

The lid 704 may be hingedly coupled to the housing 702 via a lid hinge 720. While the lid hinge is illustrated as a pin hinge, it will be appreciated that other types of hinges may be used, such as a living hinge. The lid 704 comprises an indentation 722 on the outside surface 716 that receives the protrusion 714 of the latch 708. In particular, as the lid 704 is closed, the latch 708 may pivot towards the housing 702, and the protrusion 714 may be positioned in the indentation 722. Embodiments of the indentation extend parallel to the lid front edge across a substantial portion of a front edge 730 of the lid 704. The indentation 722 may extend along a distance that is greater than 50% of the length of the font edge 730. Alternatively, indentation 722 may extend along a distance that is greater than 75% of the length of the font edge 730.

The latch may comprise an extension 732 that extends at an angle from the latch body 734. The angle between the extension 732 and the latch body 734 may be between 45 degrees and 135 degrees and may be 90 degrees. The protrusion 714 may extend downwardly from a lower surface 740 of the latch extension 732. In this manner the extension 732 overlaps with the lid front edge 730 along a portion of the lid front edge, thereby securing the front edge 730 between a top surface 738 of the housing front wall 724 and a lower surface 740 of the latch extension 732. The protrusion 714 engages the indentation 722 and secures the latch 708 against opening.

To open the lid 704, a user pulls the latch 708 and pivots it away from the housing 702, thereby releasing the protrusion 714 from the indentation 722 and allowing the lid 704 to be opened. Additionally, the lid 704 may comprise channel protrusions 726A, 726B positioned in the recessed areas 706A, 706B. As the lid 704 is opened and closed, the channel protrusions 726A, 726B may pivot in the recessed areas 706A, 706B. In some embodiments, the lid 704 may not have channel protrusions. It will be appreciated that the housing 702 may be resistant to or sealed against contaminant ingress to enable easy cleaning and to obstruct contamination from penetrating the housing 702 and contacting electrical components within the housing 702.

FIGS. 28-34 illustrate an indicator device in a closed position. The indicator device may comprise grips positioned on both sides. The grips may protrude from both sides of the indicator device. However, in some embodiments, the grips may be channels that are recessed on both sides of the indicator device. In some embodiments, the grip channels may be formed from a mold and be part of the indicator device. It will be appreciated that the grip channels assist a user when securing or removing the indicator device from an absorbent article. Furthermore, in FIGS. 35-41, the indicator device is shown in an opened configuration.

While the present invention has been described with reference to one or more particular embodiments, those skilled in the art will recognize that many changes may be made thereto without departing from the spirit and scope of the present invention. Furthermore, components from one embodiment can be used in other non-exclusive embodiments. Each of these embodiments and obvious variations thereof is contemplated as falling within the spirit and scope of the invention.

What is claimed is:

1. A sensor system for sensing wetness in an absorbent article, the sensor system comprising:
   an indicator device that is attached to the absorbent article, the indicator device comprising an outer housing, an inner housing, and a hinge portion; and
   a fastener that connects the outer housing and the inner housing and that secures the housing to the absorbent article;
   wherein the indicator device produces a first indication to indicate that the indicator device has been properly attached to the absorbent article, and the indicator device produces a second indication to indicate that the indicator device has not been properly attached to the absorbent article; and
   wherein the indicator device being properly attached to the absorbent article comprises the indicator device being electrically connects with a plurality of conductive strips placed between a topsheet and a backsheet of the absorbent article; and
   wherein the outer housing comprises one or more size indicator lights.

2. The sensor system of claim 1 wherein the first indication comprises illuminating a light.

3. The sensor system of claim 2 wherein the second indication comprises illuminating a second light.

4. The sensor system of claim 1 wherein the first indication comprises illuminating a light having a first color.

5. The sensor system of claim 4 wherein the second indication comprises illuminating a light having a second color different from the first color.

6. The sensor system of claim 1 wherein the first indication comprises emitting a first audible acknowledgment.

7. The sensor system of claim 6 wherein the second indication comprises emitting a second audible acknowledgment different from the first audible acknowledgment.

8. The sensor system of claim 1 wherein the one or more size indicator lights illuminate to indicate the size of the absorbent article after the indicator device is properly attached to the absorbent article.

9. The sensor of claim 8 wherein the one or more size indicator lights illuminate automatically upon attachment of the indicator device.

10. The sensor of claim 8 wherein the outer housing further comprises a button.

11. The sensor of claim 10 wherein the one or more size indicator lights illuminate after the button has been actuated.

12. The sensor system of claim 1 wherein the indicator device transmits information regarding the diaper size to a remote display device.

13. The sensor system of claim 12 wherein the remote display device comprises a software application running on a mobile electronic device.

14. A sensor system for sensing wetness in an absorbent article, the sensor system comprising:
   an indicator device that is attached to the absorbent article, the indicator device comprising an outer housing, an inner housing, and a hinge portion; and
   a fastener that connects the outer housing and the inner housing and that secures the housing to the absorbent article;
   wherein the indicator device produces a size indication indicating a size of the absorbent article when the indicator device has been properly attached to the absorbent article; and
   wherein the indicator device being properly attached to the absorbent article comprises the indicator device being electrically connects with a plurality of conductive strips placed between a topsheet and a backsheet of the absorbent article.

15. The sensor system of claim 14 wherein the size indication comprises a first light that illuminates when the absorbent article has a first size.

16. The sensor system of claim 15 wherein the size indication comprises a second light that illuminates when the absorbent article has a second size.

17. The sensor system of claim 14 wherein the size of the absorbent article corresponds to a distance between the plurality of conductive strips.

18. The sensor system of claim 17 wherein the absorbent article first size corresponds to the conductive strips being spaced apart a first distance.

19. The sensor system of claim 18 wherein the absorbent article second size corresponds to the conductive strips being spaced apart a second distance.

\* \* \* \* \*